(12) United States Patent
Meuser et al.

(10) Patent No.: US 8,193,341 B2
(45) Date of Patent: *Jun. 5, 2012

(54) INULIN OF VERY HIGH CHAIN LENGTH

(75) Inventors: Friedrich Meuser, Berlin (DE); Ingo Bauer, Neu-Isenburg (DE); Elke Hellwege, Berlin (DE); Jens Pilling, Dortmund (DE)

(73) Assignee: Bayer Cropscience AG, Monheim (DE)

( * ) Notice: Subject to any disclaimer, the term of this patent is extended or adjusted under 35 U.S.C. 154(b) by 590 days.

This patent is subject to a terminal disclaimer.

(21) Appl. No.: 12/298,689

(22) PCT Filed: Apr. 27, 2007

(86) PCT No.: PCT/EP2007/004028
§ 371 (c)(1),
(2), (4) Date: Oct. 27, 2008

(87) PCT Pub. No.: WO2007/128559
PCT Pub. Date: Nov. 15, 2007

(65) Prior Publication Data
US 2009/0099129 A1 Apr. 16, 2009

Related U.S. Application Data

(60) Provisional application No. 60/796,818, filed on May 2, 2006, provisional application No. 60/855,248, filed on Oct. 30, 2006.

(30) Foreign Application Priority Data

Apr. 28, 2006 (EP) .................................. 06090066
Oct. 27, 2006 (EP) .................................. 06090199

(51) Int. Cl.
*C07H 1/00* (2006.01)
(52) U.S. Cl. .................................................. 536/123.1

(58) Field of Classification Search .................. None
See application file for complete search history.

(56) References Cited

U.S. PATENT DOCUMENTS

| 1,616,164 A | 2/1927 | Arsem | |
|---|---|---|---|
| 1,616,167 A | 2/1927 | Arsem | |
| 6,569,488 B2* | 5/2003 | Silver | 426/658 |
| 7,959,962 B2* | 6/2011 | Hellwege et al. | 426/549 |

FOREIGN PATENT DOCUMENTS

| WO | WO 99/24593 | 5/1999 |
|---|---|---|
| WO | WO 2006/108697 | 10/2006 |
| WO | WO 2007/128558 | 11/2007 |
| WO | WO 2007/128560 | 11/2007 |

OTHER PUBLICATIONS

Cooper and Carter "Anti-complementary Action of Polymorphic 'Solubility Forms' of Particulate Inulin." Molecular Immunity 23(8): 895-901, 1986.

López-Molina, et al. (Jun. 2005) "Molecular Properties and Prebiotic Effect of Inulin Obtained from Artichoke (*Cynara scolymus* L.)" Phytochemistry 66(12): 1476-1484.

Moerman, et al. (2004) "Enrichment of Higher Molecular Weight Fractions in Inulin." Journal of Agricultural and Food Chemistry 52(12): 3780-3783.

Scott (1931) "Morphological and Chemical Studies on the Globe Artichoke, *Cynara scolymus* L." Proceedings of the American Society for Horticultural Science 27: 356-359.

Wack and Blaschek (2006) "Determination of the structure and degree of polymerisation of fructans from *Echinacea purpurea* roots." Carbohydrate Research 341: 1147-1153.

* cited by examiner

*Primary Examiner* — Elli Peselev
(74) *Attorney, Agent, or Firm* — Hunton & Williams, LLP

(57) ABSTRACT

The invention relates to a long-chain inulin and its preparation from artichoke roots, to its use in foodstuffs and cosmetic preparations and to foodstuffs and cosmetic preparations which comprise the long-chain inulin.

32 Claims, 12 Drawing Sheets

A = washed roots
B = Extract after not extration

B = Extract
C = Precipitated inulin
D = Upper run of the inulin precipitation

C = Inulin after precipitation at 4°C
E = Clear phase after 1st reprecipitation
F = Sedimented inulin after 1st reprecipitation

US 8,193,341 B2

INULIN OF VERY HIGH CHAIN LENGTH

CROSS-REFERENCE TO RELATED APPLICATIONS

This application is the U.S. National Stage filing of International Application No. PCT/EP2007/004028, filed Apr. 27, 2007, which claims priority to EP 06090066.9, filed Apr. 28, 2006; U.S. Provisional Patent Application No. 60/796,818, filed May 2, 2006; EP 06090199.8, filed Oct. 27, 2006; and U.S. Provisional Patent Application No. 60/855,248, filed Oct. 30, 2006, the disclosures of each of which are hereby incorporated by reference.

BACKGROUND OF THE INVENTION (i) Field of the Invention:

The invention relates to a particularly long-chain inulin and its preparation from artichoke roots, to its use in foodstuffs and cosmetic preparations and to foodstuffs and cosmetic preparations which comprise the particularly long-chain inulin.

(ii) Description of the Related Art:

The demand for foodstuffs which contain little fat and more natural raw materials has increased greatly in recent decades. Many substances have already been proposed as substitute for fats, such as products based on carbohydrates or protein or synthetic fat substitutes such as sugar polyesters of fatty acids. However, these always have disadvantages such as a low thermal stability, an unsatisfactory "mouth feel" or an unwanted effect on people or the environment.

It has been known for a long time that inulin is suitable for use in food products. Inulin has a low energy value available for humans and thus use of inulin as fat substitute ensures a large reduction in the calorific value of the final product. In addition, inulin is used as prebiotic addition and bulking agent in foodstuffs.

Inulin is a polysaccharide belonging to the fructan group. It consists of a beta-2-1-linked chain of fructose molecules, and this chain may have an alpha-D-glucose unit at the reducing end. Inulin occurs in economically recoverable amounts in various plants such as, for example, chicory roots, Jerusalem artichoke and dahlia tubers. The average chain lengths of the various inulins and their physicochemical properties differ from plant species to plant species.

The inulins employed to date in the foodstuffs sector are not entirely satisfactory in their processing properties such as, for example, viscosity in aqueous pasty form, thermal stability and stability to acid, emulsifiability and water-binding capacity.

There is in addition a need for inulins with improved fermentation properties and a greater prebiotic effect.

A further problem is that on extraction of inulin with hot water from the plant tissue the extract contains besides the polymer crude inulin also monosaccharides such as glucose and fructose, disaccharides such as sucrose and fructooligosaccharides (DP 3-10). These by-products (mono- and disaccharides, fructooligosaccharides (DP 3-10) may interfere with further processing of the inulin. For example, mono- and disaccharides are undesired in the manufacture of dietetic food products. The sweet taste of the mono- and disaccharides and fructooligosaccharides (DP 3-10) interferes with certain applications in the food products sector. Fructooligosaccharides (DP 3-10) may, because of their hygroscopicity and tackiness, interfere greatly with the use of crude inulin in food products both during processing and during storage. During further processing of the crude inulin, for example by chemical derivatization, mono- and disaccharides and fructooligosaccharides (DP 3-10) may lead to undefined mixtures of products which can be purified only by costly methods or not at all. In addition, a high proportion of reducing sugars has the disadvantage that in thermal processes in the presence of amino compounds there may be unwanted browning reactions, the formation of off-flavors and the production of acrylamide (Maillard reaction).

SUMMARY OF THE INVENTION

The present invention is based on the object of providing an inulin with which it is possible to solve the problems defined above.

The intention was in particular to achieve advantageous processing properties for applications in cosmetics and the foodstuffs industry. Examples thereof are an advantageous viscosity behavior, a high thermal stability and stability to acid, a good emulsifiability and a high water-binding capacity.

One problem addressed by the invention was additionally to provide an inulin having improved fermentation properties and improved prebiotic effect for foodstuffs applications.

Finally, it was desirable to provide an inulin which, by comparison with crude inulin, has a smaller content of mono- and disaccharides and of fructooligosaccharides (DP 3-10).

The foregoing problems are solved by the provision of the embodiments defined in the claims.

DETAILED DESCRIPTION OF THE INVENTION

The present invention relates to an inulin which has an average degree of polymerization $DP_w$ of between 65 and 81, preferably between 65 and 79, even more preferably between 66 and 78, very particularly even more preferably between 66 and 76, yet more preferably between 66 and 74 and most preferably between 66-73.

In this connection and in connection with the present invention, the term "between" is also intended to include the respectively indicated numerical limits.

The term "inulin" is intended to mean in connection with the present invention a polyfructan which consists of a beta-2-1-linked chain of fructose molecules. This chain preferably has at its end a reducing alpha-D-glucose unit.

In connection with the present invention, the term "average degree of polymerization $DP_w$" (average DP weight) means the quotient of the weight-average molecular mass $M_w$ and the molecular mass of the monomer $M_o$. The weight-average molecular mass $M_w$ results from $$M_w = \frac{\sum N_i M_i^2}{\sum N_i M_i},$$

where Ni is the number of molecules with molecular mass Mi.

The "average degree of polymerization $DP_w$" is preferably measured in connection with the present invention by the method of "gel permeation chromatography with light scattering and refractive index detection (GPC-RI-MALLS system)" described hereinafter.

The inulin of the invention exhibits, by comparison with inulins described in the prior art, the surprising advantage that it can be processed to creams which exhibit unusually high stability on heat treatment or acid treatment, so that they are more suitable for example for particular industrial applications or applications in the cosmetics and/or food products industries. In addition, creams comprising the inulin of the invention show an unexpectedly high stability toward shear forces. The inulin of the invention thus exhibits the further advantage, compared with conventional inulin, that it can be processed better in industrial processes in which strong shear forces act.

The inulin of the invention is further notable for particularly advantageous viscosity properties and a high gel strength and a very low solubility, which is advantageous for foodstuffs applications.

In addition, the inulin of the invention shows surprisingly good properties as fat substitute in foodstuffs with excellent sensory properties in the mouth.

The inulin of the invention also shows by comparison with previously employed products a slower fermentation, which is advantageous in the prevention of diseases in the posterior large bowel. The slower fermentation is accompanied by a reduced formation of gas in the bowel, especially of hydrogen.

The inulin of the invention additionally has by comparison with previously employed products a greater prebiotic effect. In particular, the inulin of the invention stimulates the generation of bifidobacteria in an advantageous manner with a simultaneous reduction of unwanted and/or pathogenic bacteria. The inulin of the invention is therefore suitable for use in foodstuffs and/or medicaments for the prevention and treatment of bowel dysfunctions and diseases, especially in the posterior large bowel.

Finally, the inulin of the invention also confers on various foodstuffs advantageous use properties such as, for example, viscosity increase, emulsifiability, water-binding capacity and crumb formation. The inulin of the invention surprisingly confers improved baking properties on bakery products and increases the dough yield. The inulin of the invention is moreover an effective means for flavor modification and foam stabilization.

In a further embodiment, the inulin of the invention has a content of fructooligosaccharides (oligofructans) having a DP of from 3 to 10 which is less than 3%, preferably less than 1.5%, particularly preferably less than 0.7%, very particularly preferably less than 0.3%.

In a further embodiment, the inulin of the invention has a glucose content of less than 2%, preferably less than 1%, particularly preferably less than 0.5%, very particularly preferably less than 0.2% and most preferably less than 0.1%.

In a further embodiment, the inulin of the invention has a fructose content of less than 2.5%, preferably less than 1.5%, particularly preferably less than 1.0%, very particularly preferably less than 0.3% and most preferably less than 0.15%.

In a further embodiment, the inulin of the invention has a sucrose content of less than 2%, preferably less than 1%, particularly preferably less than 0.5%, very particularly preferably less than 0.3% and most preferably less than 0.1%.

In an embodiment of the inulin of the invention which is particularly advantageous for foodstuffs applications, the content of mono- and disaccharides is less than 0.5%.

All percentages are, unless otherwise indicated, percent by weight based on the total dry weight of inulin and further substances. "Further substances" are all substances in the dry mixture which are different from inulin.

The fructose, glucose and sucrose content is measured in connection with the present invention by the optical enzymatic method described below (general methods: "sugar determination").

In a further embodiment, which may include the previous embodiments, the inulin of the invention has a weight average molecular mass $M_w$ of between 10 500 g/mol and 13 150 g/mol, preferably between 10 500 and 12 800 g/mol, particularly preferably between 10 650 g/mol and 12 650 g/mol, even more preferably between 10 650 g/mol and 12 350 g/mol and most preferably between 10 650 g/mol and 12 000 g/mol.

The weight-average molecular mass $M_w$ is preferably measured in connection with the present invention by the method of "gel permeation chromatography with light scattering and refractive index detection (GPC-RI-MALLS system)" described hereinafter.

In a further embodiment, which may include the previous embodiments, the inulin of the invention has an average degree of polymerization $DP_{n\ (GPC)}$ measured by gel permeation chromatography (GPC) of between 54 and 75, preferably between 54 and 72, even more preferably between 57 and 71, particularly preferably between 60 and 71.

The "average degree of polymerization $DP_n$" is measured in connection with the present invention preferably by the method of "gel permeation chromatography with light scattering and refractive index detection (GPC-RI-MALLS system)" described hereinafter.

In connection with the present invention, the term "average degree of polymerization $DP_n$" (mean DP number) means the quotient of the number-average molecular mass $M_n$ and the molecular mass of the bound monomer $M_o$ (anhydrofructose=162 g/mol). The number-average molecular mass $M_n$ results from $$M_n = \frac{\sum N_i M_i}{\sum N_i},$$

where $N_i$ is the number of molecules having molecular mass $M_i$.

In a further embodiment, which may include the previous embodiments, the inulin of the invention has a molecular weight distribution in the range from 650 to 48 000, more preferably 970 to 40 000 g/mol, even more preferably 1300 g/mol to 34 000 g/mol and most preferably from 4000 g/mol to 26 800 g/mol.

In yet a further embodiment, which may include the previous embodiments, the inulin of the invention shows a total mass of inulin molecules having a molecular weight of <10 000 g/mol based on the total mass of all inulin molecules of 25-40% and a total mass of inulin molecules having a molecular weight of >20 000 g/mol based on the total mass of all inulin molecules of 5-20%. It is even more preferred for the total mass of inulin molecules having a molecular weight of <10 000 g/mol based on the total mass of all inulin molecules to be 30-36% and the total mass of inulin molecules having a molecular weight of >20 000 g/mol based on the total mass of all inulin molecules to be 9-15%.

The molecular weight distribution is preferably measured in connection with the present invention by the method of "gel permeation chromatography with light scattering and refractive index detection (GPC-RI-MALLS system)" described hereinafter.

In one embodiment of the inulin of the invention with particularly advantageous properties, the degree of branching is 0.5-2.0 mol %, more preferably 0.7-2.0 mol %, even more preferably 0.9 to 2.0 mol % and most preferably 1.1 to 2.0 mol %. The degree of branching is defined herein as the percentage number of beta-2-1-linked fructose monomers with additional branch point at position 6 of the fructose monomer (also abbreviated to "2-1,6-" hereinafter) based on the total number of all inulin monomers measured in a sample of the inulin of the invention with randomly distributed molecular weights. At its position 6, a "2-1,6-" fructose monomer within a polyfructose chain is linked to another polyfructose chain, consisting of at least two beta-2-1-linked fructose monomers, or to a single fructose monomer. The term "branch point" designates a position of a fructose monomer, within a polyfructose chain, to which another polyfructose chain consisting of at least two beta-2-1-linked fructose monomers, or a single fructose monomer is linked. The degree of branching is measured by the method of standard methylation analysis or alternatively by the method of reductive degradation after methylation. Both methods are described in detail in the appended examples.

An embodiment of the inulin of the invention which is particularly advantageous in its properties and which may include the previously described embodiments has a particularly narrow molecular weight distribution expressed by the quotient between the weight average degree of polymerization and the number average degree of polymerization DPw/DPn. This quantity is also referred to as polydispersity index. In a preferred embodiment, the quotient DPw/DPn is less than 1.25, in a more preferred embodiment is less than 1.20, in an even more preferred embodiment is less than 1.15 and in the most preferred embodiment is less than 1.10. The values for DPw and DPn are in this connection measured by the method of "gel permeation chromatography with light scattering and refractive index detection (GPC-RI-MALLS system)" described hereinafter. The molecular weight of a monomer for conversion calculations is set equal to 162 g/mol.

The invention further relates to an aqueous paste of the inulin of the invention which is obtainable by dispersing the inulin in water, shearing the resulting dispersion until homogeneous, storing the product obtained in this way at 4-15° C. for 12-24 h and, after conditioning to room temperature, stirring to give a homogeneous paste. A preferred paste comprises water and 1-40% by weight, more preferably 1-35% by weight, still more preferably 1-30% by weight, even more preferably 2-25% by weight, yet more preferably 2-20% by weight, and particularly preferably 10-20% by weight inulin based on the total weight of the paste. The term "paste" is according to this invention equivalent to a suspension of cristalline and/or amorphous inulin. Accordingly, the term "aqueous paste" is to be understood as a suspension of cristalline and/or amorphous inulin in aqueous phase. The aqueous phase is based on water which can optionally comprise further dissolved or suspended substances, such as salts, other carbohydrates, proteins, amino acids. In an advantageous embodiment the inulin in the paste is a spray dried inulin, i.e. an inulin which was spray dried before forming the paste.

The above described paste can be used as a component in aqueous systems. Preferred aqueous systems are foodstuffs on aqueous basis and cosmetics, wherein the term "foodstuff" is defined elsewhere in the present description. Examples of preferred foodstuffs are also listed elsewhere in the present description. In foodstuffs and cosmetics, a paste according to the invention can be used as structure imparting component, thickening agent, texturizing agent, stability enhancing agent or viscosity-building agent, wherein the paste in this connection can fulfill one or more of the above mentioned functions. In foodstuffs, a paste according to the invention can also be used as a fat substitute, oil substitute, prebiotic agent and/or dietary fiber component, wherein the paste in this connection can fulfill one or more of the above mentioned functions. The most preferred use is the use as an oil or fat substitute. The most preferred foodstuffs wherein a paste according to the invention is used as a component, are dairy products, such as yoghurt, yoghurt drinks, cream, crème fraiche, curd, butter, milk, especially skim milk, buttermilk, soured milk, kefir, cheese, such as cream cheese, soft cheese, sliced cheese, hard cheese, whey, milk powder, drinks on milk basis.

The inulin of the invention shows a surprisingly high stability to acid. In particular, an aqueous paste of the inulin of the invention shows a high stability to acid. The shear stability of an aqueous inulin paste of the invention is likewise exceptional by comparison with commercially available products.

The inulin of the invention is distinguished from other, commercially available inulins by a surprisingly high gel strength. Gel strengths of 4-100 N, more advantageously 10-100 N, even more advantageously 20-100 N and most advantageously 40-100 N, are achieved at a concentration of 1-35% (w/w), more preferably 1-30% (w/w), still more preferably 2-25% (w/w), yet more preferably 2-20% (w/w), most preferably about 20% (w/w) of the inulin of the invention in water when inulin is dissolved at 90° C. and then stored at room temperature (23° C.) for a period of 24 h. High gel strengths as indicated previously can be attained particularly well with inulins of the invention which are spray dried and then employed for gel formation. The gels obtained in this way preferably show a particulate character (particle gels). The measurement method for determining the gel strength is described in detail in the examples section (structure formation by inulins after heating in water).

The present invention relates in a further aspect to a process for obtaining inulin in which
a) artichoke roots are comminuted
b) an extract is obtained by treating the comminuted roots with water,
c) coloring constituents are removed from the extract obtained,
d) inulin is precipitated from the extract,
e) the inulin is reprecipitated at least once.

The process is particularly suitable for obtaining the previously described inulins of the invention, but is not restricted thereto.

Artichoke roots are used as starting material, but the process is not restricted to a particular variety. The comminution is advantageously preceded by removing any adherent contaminants from the roots, e.g. by vigorous washing with water with a high-pressure cleaner. It is advantageously possible to wash the roots in the deep-frozen state in order to minimize the loss of mass of root material.

If necessary, the roots are initially comminuted coarsely, e.g. by chopping. Shredders are preferred for the further comminution. The product obtained is comminuted root material in the form of fibrous chips.

In the most advantageous embodiment of the process, artichoke roots with the following characteristics are used: ripe roots with respect to the formation of dry mass and inulin. The degree of ripeness can be established from the ratio of inulin content to dry matter content and the ratio of fructose content to inulin content. The inulin content is preferably in the range of 30-70% by weight, more preferably 40-65% by weight, still more preferably 50-60% by weight, based on total weight of dry matter of roots, and the fructose/inulin ratio is preferably in the range of 3-24% by weight, more preferably 3-12% by weight, most preferably lower than 6% by weight. The dry matter content of the cleaned artichoke roots is preferably 20-50% by weight, more preferably 30-40% by weight, more preferably 30-35% by weight, based on the total weight of cleaned roots.

In case that artichoke roots must be stored before using them in the process of the present invention, the roots should be conserved in order to prevent microbial contamination, rotting or decrease of molecular weight of inulin due to enzymatic degradation. Preferred methods for conservation of the roots are freezing or hot air drying of comminuted roots for storage.

After the comminution, the comminuted root material is extracted with water, preferably at a temperature of 60° C. to 95° C., most preferably 80-95° C. The extraction preferably takes place in the neutral to slightly alkaline pH range. A temperature of at least 60° C. at pH 7-9 is advantageous because in this case enzymatic and acidic hydrolysis are suppressed. The concentration of comminuted root material in the water is preferably 10-40% by weight, more preferably 20-30% by weight, measured as fresh weight of roots based on the total weight of the extraction mixture.

Preferably a ratio between the dry matter of the shredded material used and the water as extraction medium is established which leads to a dry matter content in the extract of 8-12% by weight and an inulin content of more than 6% by weight, preferably 6-8% by weight, based on the weight of the extract. A correspondingly suitable choice of extraction conditions, such as the ratio of water to root weight, can lead to a transfer of 80-90% by weight of the inulin present in the roots into the extract. The aforementioned conditions are suitable to achieve a favorable crystallization and a high yield of the inulin from the extract, based on the observation that the high molecular weight inulin crystallizes from the extract even at a concentration as low as 5% by weight, based on the weight of the extract.

There is no special restriction on the extraction equipment, and conventional extraction techniques for plant material can be applied. It is most preferred according to the invention for the extraction to take place in a jacket-heated extractor with agitator. In another highly preferred embodiment a heatable lauter tun is used as stirred extractor. Thus, the extraction of the inulin from the roots is combined with the separation of the extract from the spent chips by filtration, as described below. The extraction time after equilibration of the root/water mixture is preferably 30 min-4 hours, preferably 1-2 hours. After this time, the extract is separated from the spent chips, e.g. by pumping off or straining off or filtration.

After separation of the extract from the spent chips, where appropriate, fibrous materials and plant fragments may remain as suspended materials in the extract. If present, these suspended materials are likewise removed from the extract. In this variant of the process, step b) of the process is thus followed, before step c), by a step in which suspended materials, mainly consisting of fibers, are removed from the extract. The acceptable amount of suspended materials and whether removal is to take place will be decided by the skilled worker from case to case. Removal of the suspended materials can take place by conventional separation techniques, as centrifugation or filtration. A desludging separator has proved particularly suitable. A screen or filter with appropriate fineness can also be used.

In a highly preferred embodiment, the suspended material can be filtered off by using the spent chips as a filter material. In this embodiment the spent chips are precipitated at the bottom of the extraction vessel equipped with a sieve at the bottom, like a lauter tun. The sieve is preferably a slit sieve. The precipitated spent chips are used as a filtration bed through which the extract flows. By using this technique a nearly quantitative removal of suspended material is possible without using further filtration steps before further refining or brightening the extract or crystallizing the inulin.

The extracts are colored owing to their content of coloring constituents and colloidally suspended colorized matter. The coloring constituents consist, inter alia, of tannins and flavanoids and usually confer a yellow or brownish yellow and/or dark brownish color on the extract. The inulins which can be obtained directly from such extracts do not comply with the desired requirements concerning a neutral color. It is therefore necessary to remove the coloring constituents from the extract in step c) of the process. Process step c) of the invention for removing coloring constituents from plant extracts is generally also referred to as decolorization, clarification or "brightening" of plant extracts. These terms are equivalent in the context of the present invention.

The brightening can take place according to the invention by adding lime and subsequent carbonation ($CO_2$ addition). The process of lime addition is known from the prior art and is used for example in obtaining sucrose from sugar beet. In an alternative brightening process, the interfering constituents are removed using an ion exchanger.

In a particularly advantageous embodiment of the process, the coloring constituents are removed in step c) by
i) admixing magnesium ions ($Mg^{2+}$) to the plant extract,
ii) admixing at least one alkaline component to the plant extract,
iii) forming a precipitate, and
iv) removing the precipitate which has formed from the plant extract.

Steps i)-iv) in this particularly preferred variant are substeps of process step c).

This process variant surprisingly makes more effective decolorization of the extract possible compared with the lime brightening process. In addition, the auxiliaries employed, magnesium salts and alkalis, are low-cost. The process is thus less costly than the use of an ion exchanger. The expenditure on apparatus and time for carrying out this process step is also particularly low. Finally, this type of brightening also simultaneously removes materials causing turbidity from the extract.

Magnesium ions ($Mg^{2+}$) are admixed according to the invention to the aqueous plant extract. It is possible in a variant of step i) to add an aqueous solution of a magnesium salt to the plant extract. In a further, more preferred variant, a magnesium salt is added directly in solid form to the plant extract and dissolved therein.

If a magnesium salt is added, it is preferably a salt which, owing to its high solubility product, is very readily soluble in water. Particularly suitable magnesium salts are selected from magnesium chloride, magnesium sulfate, magnesium nitrate, magnesium salts of lower fatty acids such as magnesium acetate and propionate, and mixtures thereof.

An alkaline component in ii) means according to the invention a component which comprises hydroxide ions ($OH^-$) or forms hydroxide ions in the extract after combining with the plant extract. The alkaline component may be liquid, solid or gaseous. A liquid alkaline component is preferably employed.

On addition of magnesium ions and an alkaline component as described in steps i) and ii) of the process, a precipitate is formed by a precipitation reaction. Steps i) and ii) can in the context of the present process in principle be carried out simultaneously, especially if a solution of magnesium ions is used in step i) and an alkaline liquid is used in step ii). However, it is preferred to carry out process step i) first and then step ii).

It is advantageous for process step c) that both the magnesium ions and the alkaline component are distributed as homogeneously as possible in the extract so that the precipitation reaction in the extract is also homogeneous and as quantitative as possible. It is therefore preferred to employ as alkaline component aqueous alkaline liquids such as, for example, alkaline solutions or alkaline suspensions which can be rapidly and homogeneously mixed into the plant extract. An alkaline solution or suspension comprises according to the invention hydroxide ions (OH⁻) or forms them after combining with the plant extract.

In a very preferred process variant, a magnesium salt is homogeneously dissolved in the extract first in step i). Subsequently, in step ii), an aqueous alkaline solution or suspension is added.

In one embodiment, the alkaline component is an aqueous solution or suspension of an alkali metal or alkaline earth metal hydroxide. The hydroxide is preferably selected from the hydroxides of the alkali metals and alkaline earth metals, such as lithium hydroxide, sodium hydroxide, potassium hydroxide, calcium hydroxide and barium hydroxide.

In a very particularly preferred variant, the alkaline component is a suspension of calcium hydroxide. The advantage of using calcium hydroxide is that a particularly small amount of centrifugate is obtained in step iii). In addition, the simultaneous precipitation of magnesium hydroxide and calcium sulfate achieves a greater sedimentation rate and a greater compressibility of the precipitate. The precipitate has particularly little gelatinous consistency. The binding of inulin in the precipitate thus remains particularly low in this process variant.

A further alkaline component which can be used is ammonia, preferably in aqueous solution. Nor is it excluded in principle to use gaseous ammonia, but this is less preferred than the use of an aqueous solution.

In a further embodiment, the alkaline component is an aqueous solution or suspension of an organic base such as ethylenediamine and triethanolamine.

Salts of weak organic acids such as alkali metal and alkaline earth metal acetates, especially sodium acetate, potassium acetate, calcium acetate and magnesium acetate, can also be used.

Magnesium hydroxide is formed as precipitate. The coloring constituents of the aqueous extract remain according to the invention in the precipitate and are thus separated from the liquid phase. A substantially decolorized extract is obtained. The amounts of $Mg^{2+}$ ions and alkaline component employed, and thus the amount of precipitate formed, determine inter alia how quantitative the decolorization is. Optimization of the amounts of the reactants is within the competence of a skilled worker. In case of magnesium sulfate, the preferable concentration is in the range of 0.5-3% by weight, more preferably 0,5-2% by weight of the aqueous extract.

In the preferred variant of step c), as described above, the molar ratio of hydroxide ions to magnesium ions $OH^-:Mg^{2+}$ is preferably from 2.2:1 to 1.8:1. It is most preferred for the ratio to be exactly stoichiometric, i.e. $OH^-:Mg^{2+}=2:1$. The amount of alkaline component is thus to be chosen so that the appropriate amount of hydroxide ions is present for the magnesium ions.

The dissolving of the magnesium salt and admixing of the alkaline component in process steps i) and ii) preferably takes place with stirring in order to achieve dissolution and homogenization as quickly as possible and thus a fast reaction. However, there are no particular further restrictions on the mixing technique. Thus, the process can be carried out for example also by other mixing techniques familiar to the skilled worker.

To expedite the process, step i) is preferably carried out at a temperature of 60-80° C. The reaction time after addition of the alkaline component is generally from about 1 to 15 min, averaging about 10 min.

The removal step iv) preferably takes place by sedimentation or filtration. The sedimentation can be made faster by a centrifuge, preferably a disk centrifuge, in particular a desludging centrifuge. However, other separation techniques familiar to the skilled worker can also be used. These can also be carried out in combination with one another, e.g. centrifugal desludging of the brightened extract with subsequent filtration of the desludged extract, e.g. with a plate filter.

The whole of step c) of the process of the invention may if required also be carried out more than once. If the previously described preferred variant of step c) with substeps i)-iv) is used, it is also possible for the individual substeps i)-iv) to be carried out more than once.

After step c), inulin is precipitated from the extract in step d). The precipitation can be effected for example by adding alcohols such as ethanol, methanol or isopropanol. In this case, depending on the amount of alcohol added or adjusted polarity of the liquid phase, initially high molecular weight inulin fractions are precipitated, so that it is possible to influence, via the amount of alcohol added, how quantitatively the inulin present in the extract is precipitated and which molecular weight fractions are predominantly obtained. Besides alcohol, it is also possible to employ other nonpolar organic liquids which are miscible with water.

For this purpose, in a particularly advantageous embodiment of this process step, to limit the use of alcohol, especially ethanol and isopropanol, the prepared extract is initially concentrated, preferably to one fourth to one fifth of its initial volume. The concentration can take place by evaporation or membrane filtration and a combination of both processes. Care must be taken in this case that the concentrate is kept hot during the concentration, preferably at 60-95° C., in order to avoid precipitation of the inulin. An advantage of membrane filtration is the depletion, associated therewith, in low molecular weight substances accompanying the inulin. The subsequent precipitation of the inulin from the concentrate can be managed by the choice of increasing alcohol concentration so that the inulin is fractionated according to molecular size ranges which are characterized for example by the weight average degree of polymerization (DPw). Depending on the choice of the precipitation conditions, the result is fractions which have the DPw according to the invention. Depending on the desired purity.

It is more preferred to obtain inulin by cooling the extract than by alcoholic precipitation. The preferred conditions are such that the extract is cooled to a temperature of 2-10° C., more preferably 2-8° C., and kept at this temperature over a period of from 6 to 140 h, preferably 6 to 48 h, during which the inulin precipitates. The cooling rate and temperature, and the duration of the cooling influence the precipitation of the inulin from the extract and the breadth of the molecular weight distribution and thus at the same time the quantity. Choice of a longer period and lower temperature results in precipitation of more low molecular weight inulins and a broader molecular weight distribution and thus a lower average molecular weight of the precipitated fraction. The precipitated inulin is separated from the liquid phase by conventional separation techniques such as, for example, centrifugation, decantation, filtration.

In a preferred embodiment, inulin is crystallized for the first time after the extraction step b) and before step c) of the above described process. Such crystallisation is preferably done as described previously. Crystallisation before step c) leads to an increase in the yield of high molecular weight inulin compared with direct brightening of the extract, and economizes the use of the brightening agents, i.e. magnesium compound and the alkaline component. It is advantageous to brighten the extract after the first crystallisation of the inulin as in this case only the coloring constituents bound to the inulin crystals have to be removed, which leads to a similarly smaller amount of inulin bound to the brightening sludge.

A first precipitation and removal of the precipitated inulin can be followed by renewed cooling of the extract or addition of alcohol in order to obtain any inulin fractions which are still dissolved. A decision about repetition is made from case to case according to how quantitatively the inulin is to be obtained from the plants and what molecular weight distribution in the final product is desired.

The inulin concentration in the extract depends substantially on the inulin content of the roots and the concentration of the comminuted roots in the extract and is a further variable which has an effect on the precipitation of the inulin by cooling the extract. The dependence of the precipitation on the concentration can therefore be utilized in order to concentrate the liquid phase after the first precipitation, e.g. by evaporation, in order also to precipitate the low molecular weight fractions if this is desired.

In the last process step e), the precipitated inulin is reprecipitated. "Reprecipitation" means in the context of this invention that the solid inulin, resulting from the previous process step, is redissolved and then precipitated and/or crystallized out of the solution again. Thus, process step e) can also be worded as: the inulin is dissolved and precipitated and/or crystallized again, wherein this step is done at least once. The crystallization differs from the precipitation in that predominantly crystalline structures are obtained.

The inulin is preferably dissolved under the influence of heat and preferably in water. Water with a temperature of 70-100° C., in particular 90-100° C., is particularly suitable.

The precipitation in step e) can take place by alcoholic precipitation as previously described. However, the inulin is preferably obtained by cooling the solution to 2-10° C., more preferably 2-8° C., over a period of 6 to 140 h, preferably 6 to 48 h.

The precipitation of the inulin dissolved in step e) can be repeated in order to obtain the inulin still remaining in the liquid phase. A decision about repetition is to be made from case to case according to how quantitatively the inulin is to be obtained from the plants and what molecular weight distribution in the final product is desired. The liquid phase can be concentrated in order to simplify the precipitation.

After reprecipitation, the resulting inulin solid is separated from the liquid phase by conventional separation techniques such as, for example, centrifugation, decantation, filtration.

In order to influence the molecular mass distribution and purity of the resulting inulin product, process step e) can be carried out more than once. It has emerged that the averages of the molecular weight and the averages of the degree of polymerization are shifted to higher values on repetition of the reprecipitation step e). It is thus possible to set various averages of the molecular weight/degree of polymerization of the inulin of the invention within the claimed range.

If fine-particle impurities are still present, it is advantageous to insert one or more filtration steps into the process. Any fine-particle impurities present are removed in the filtration. The fineness of the filter is chosen by the skilled worker depending on the particle size of the impurity.

The filtration step(s) can be inserted anywhere in the process after obtaining the extract. A filtration step directly after obtaining the extract in step b) for example is advantageous. The filtration step is to be distinguished from the removal of suspended materials as described previously, because the particles removed by the filtration are finer than the suspended materials, which consist mainly of fibers. In a further preferred embodiment, the filtration step is carried out before step d).

The filtration step is preferably combined with a reprecipitation as described for process step e). This entails the inulin being dissolved as previously described for step e), and the solution then being filtered. After the filtration, the inulin is precipitated or crystallized out of the filtered solution. The solid inulin resulting after the precipitation or crystallization can be separated from the liquid phase by conventional separation techniques, such as, for example, centrifugation, decantation and filtration.

In some cases the resulting inulin can be discolored by substances which can not be removed by filtration. In such cases it is preferred to remove the coloring impurities by a treatment with activated carbon. In one embodiment active charcoal is suspended in water and added to an inulin solution at a temperature of above 80° C., preferably above 90° C. In case of a 20% by weight inulin solution the amount of active carbon is preferably in a range of 1-10% by weight, preferably 2-6% by weight, more preferably 2-3% by weight, based on the weight of the inulin solution. After adsorption of the coloring impurities, the activated carbon is removed by centrifugation and/or filtration. The activated-carbon suspension can be preclarified by centrifugal separation of the activated-carbon sludge and then clarified by two-stage filtration, for example with a combination of a kieselguhr precoat filter and a sheet filter. It is important that during the separation of the active charcoal from the inulin solution the temperature is maintained above 80° C., preferably above 90° C., in order to keep the inulin in solution. After removal of the active charcoal, the inulin can be precipitated or crystallized and separated from the liquid phase as described above.

After separation from the liquid phase, the final product can be washed again with water or a water/alcohol mixture. Washing with cold water at a temperature of 2-10° C. is preferred. For this purpose, the inulin precipitate is slurried in water and the inulin is then sedimented again.

The resulting inulin is preferably dried in a further, last process step. The drying can take place by freeze drying, spray drying or drum drying.

In a preferred embodiment, the inulin of the invention is in spray-dried form. Suitable spray-drying parameters are described in the appended examples. It is self evident that in case of a spray drying process a precipitated or crystallized inulin must be brought into suspension (in water below about 80° C.) or into solution (in water above about 80° C.) again. Alternatively, a last precipitation or crystallization step, as described above, can be omitted and the suspended or dissolved inulin from the process can directly be spray dried. It is possible by adding spray-dried inulins of the invention to liquid prepared food products for the viscosity to be increased particularly effectively. On addition of equal quantities of inulin of the invention, a greater increase in viscosity is achieved with a spray-dried inulin compared with an inulin dried in another way (e.g. freeze drying).

In yet a further preferred embodiment, the inulin of the invention is in spray-granulated form. Spray-granulated inulin is obtained by known processes, e.g. by introducing a previously spray-dried material as granulation seed and spray drying further inulin. An inulin with a particle size of 10-100 µm for example can serve as initial charge. Suitable spray-granulation conditions are for example a feed composition of 70% water and 30% inulin and a feed temperature of 90° C.

The inulin of the invention very particularly preferably has an average particle diameter of 50-350 µm, more preferably 80-300 µm, even more preferably 100-250 µm and most preferably 100-200 µm. Such an inulin is thus a further aspect of this invention.

The average particle diameter can be determined both by sieve analysis of a dry sample and by light scattering. The preferred method is, however, sieve analysis so that the inulin of the invention preferably has an average particle diameter of 50-350 µm, more preferably 80-300 µm, even more preferably 100-250 µm and most preferably 100-200 µm, determined by sieve analysis.

In one embodiment, the inulin of the invention having the described particle sizes is obtained by spray-drying or spray-granulation process. A spray-dried or spray-granulated inulin having the previously described particle sizes is thus a further aspect of this invention.

It is possible to adjust the preferred average particle diameter of a dried inulin by means of sieve fractionation in the event that, after drying, it is still outside the preferred range. Selection of the suitable sieve size lies within the competence of the average skilled worker.

The inulin particles of the invention preferably have a crystalline fraction of less than 45%, more preferably less than 40%, even more preferably less than 35%. In a further preferred embodiment, less than 20%, even more preferably less than 10%. In the most preferred embodiment, the degree of crystallinity is less than 1%. The stated degrees of crystallinity are determined by the method of Ruland-Vonk (W. Ruland, Acta Cryst., 14, 1180 (1961); C. G. Vonk, J. Appl. Cryst. 6, 148 (1973)). The method for determining the degree of crystallinity is described in detail in the appended examples. A low degree of crystallinity confers better dissolving properties on the inulin, which is advantageous in certain foodstuff applications.

In yet a further aspect, the invention also relates to compositions which comprise the previously described inulin of the invention and one or more edible or pharmaceutically acceptable ingredients. Typical compositions include foodstuffs for humans and animals, beverages, functional foodstuffs, medicaments and pharmaceutical compositions (including prophylactic compositions and therapeutic compositions), and intermediates thereof.

A functional foodstuff means in the context of the present invention a foodstuff which apart from traditional nutrients comprises an ingredient which may have a health-promoting effect (definition of the Institute of Medicine of the National Academy of Sciences, USA, 1994).

Said edible or pharmaceutically acceptable ingredients are preferably selected from the group consisting of sugars (e.g. glucose, fructose, sucrose, lactose, galactose, maltose, isomaltose, polydextrose), polyols (e.g. sorbitol, lactitol, maltitol, isomalt, mannitol, xylitol), maltodextrins, sweeteners, hydrogenated glucose syrups, additions to human and animal foods, intermediates for human and animal foods, human and animal food products, edible liquids, beverages, bioavailable sources of minerals, pharmaceutically acceptable carriers, pharmaceutically and therapeutically active substances, pharmaceutical compositions and medicaments.

A particularly preferred composition of the present invention includes the inulin of the invention in the presence of an edible or pharmaceutically acceptable, bioavailable source of minerals, especially a source of calcium and/or magnesium and/or iron, such as, for example, dairy products and salts and complexes of calcium, magnesium and iron.

As explained above, the aim of the present invention was to provide an inulin with particularly advantageous properties for use in foodstuffs, with the terms food product and foodstuffs being equivalent according to the invention. In a further aspect, the present invention thus also relates to foodstuffs and dietary supplements which comprise the previously described inulin. The term foodstuffs include according to the present invention both foodstuffs for humans and animal foodstuffs or animal feed. The dietary supplements include dietary supplements for humans and for animals.

A particularly preferred foodstuff is selected from dairy products, yoghurts, ice creams, milk-based soft ice, milk-based garnishes, puddings, milkshakes, egg custard, cheese, nutrition bars, energy bars, breakfast bars, confectionery, bakery products, crackers, cookies, biscuits, cereal chips, snack products, ice tea, soft ice made from fruit juice, diet drinks, finished drinks, sports drinks, stamina drinks, powdered drink mixtures for dietary supplementation, infant and baby food, calcium-supplemented orange juice, bread, croissants, breakfast cereals, noodles, spreads, sugar-free biscuits and chocolates, calcium chews, meat products, mayonnaise, salad dressings, nut butter, deep-frozen meals, sauces, soups and ready-to-serve meals. The foodstuff comprising the inulin of the invention is most preferably a dairy product, especially a yoghurt. The inulin of the invention shows a particularly good effect on the stability, the texture, the body and the mouth feel of dairy products, especially yoghurt, possibilities being stirred or pot-fermented yoghurt or yoghurt drinks.

Other useful dairy products according to the present invention are cream, crème fraiche, curd, butter, milk, especially skim milk, buttermilk, soured milk, kefir, cheese, such as cream cheese, soft cheese, sliced cheese, hard cheese, whey, milk powder, drinks on milk basis.

A preferred level of inulin in foodstuffs, especially in dairy, particularly in yoghurt, is 0,2-5% by weight, preferably 0,5-4,5% by weight of dry inulin, based on the total weight of all components of the foodstuff, dairy, or yoghurt.

In one embodiment of the invention, the foodstuff is a foodstuff manufactured by an extrusion process, such as, for example, a breakfast cereal.

In a further aspect, the present invention relates to cosmetic preparations which comprise the previously described inulin. The cosmetic preparation particularly preferably takes the form of creams, in particular skin and face creams.

In a further aspect, the present invention also relates to the use of the previously described inulin as addition in foodstuffs, functional foodstuffs and cosmetic preparations. The use also relates in particular to all specific foodstuffs and cosmetic preparations as mentioned above.

In yet a further aspect, the present invention relates to the use of the inulin of the invention for the manufacture of a pharmaceutical composition or of a medicament.

The inulin of the invention can advantageously be used in foodstuffs, functional foodstuffs, pharmaceutical compositions or medicaments which serve to modify or regulate the composition of the bacterial flora in the large bowel, especially in the distal region of the large bowel, of humans, mammals and other vertebrates.

It is likewise possible to use the inulin of the invention in foodstuffs, functional foodstuffs, pharmaceutical compositions or in medicaments which serve to modify or regulate the fermentation pattern of inulin in the large bowel, especially in the distal region of the large bowel, of humans, mammals and other vertebrates.

A further preferred use of the inulin of the invention is the use as fat or oil substitute and/or as a dietary fiber in foodstuffs, wherein the term "foodstuff" encompasses at least all above mentioned foodstuffs, especially all above mentioned dairy products. It is advantageous that the sensory properties, especially the mouthfeel, are excellent compared with conventional inulins. Thus, inulin of the present invention can also be used as an enhancer of sensory properties, especially as a mouthfeel enhancer, in foodstuffs.

A further use of inulin of the invention is the use as a texturizing agent, stability enhancing agent, viscosity-building agent, especially in foodstuffs and cosmetics. The term "foodstuff" encompasses at least all above mentioned foodstuffs, especially all above mentioned dairy products.

Finally, the inulin of the invention can be used in foodstuffs, functional foodstuffs, pharmaceutical compositions or in medicaments which have the following advantageous effects: roughage effects, regulation of bowel function, prebiotic effect and/or bifidogenicity, increased absorption of minerals, e.g. of calcium, magnesium and iron, increase in bone mineral density, increase in the bone mineral content, increase in the maximum bone mass, improvement in bone structure, reduction in the loss of bone mineral density, reduction in the loss of bone structure, regulation of lipid metabolism, stimulation of the immune system, prevention of cancer and reduction of the risk of cancer, prevention of large bowel cancer and reduction of the risk of large bowel cancer and prevention of breast cancer.

Figure 1:
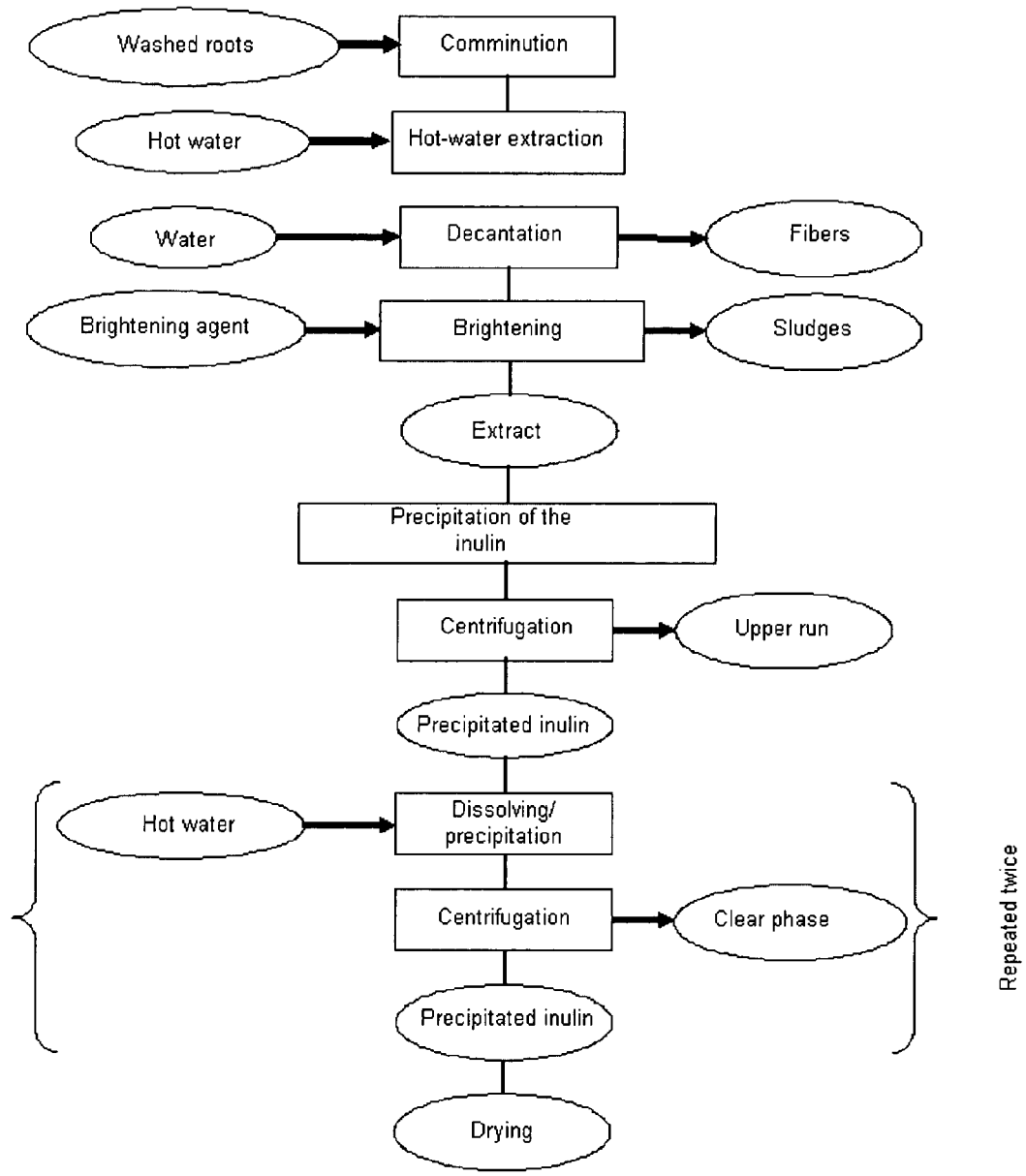
FIG. 1 shows a diagrammatic representation of the inulin extraction.

The invention is explained below by means of examples which are not intended to restrict the general inventive concept.

EXAMPLES

General Methods

1. Fructan Determination
1.1 Fructan Determination by Hydrolysis with Exoinulinase The inulin solutions to be measured are prepared by weighing 50.0+/−5.0 mg of inulin accurately into a 1 ml graduated flask. 700 µl of dd $H_2O$ are added to dissolve. The sample is then shaken in order to detach the sample material as well as possible from the base of the vessel, and is then placed in an almost boiling waterbath (~99° C.) for 8 min. During the incubation, the graduated flask is shaken every 30 seconds. After the incubation, the sample is allowed to cool to room temperature and is then made up to the 1 ml mark with dd $H_2O$. The sample solution has an inulin concentration of 5.0+/−0.5%.

For sugar determination before the digestion, 200 µl are removed and frozen at −20° C. Before the sugar measurement, this sample is thawed at room temperature, mixed, dissolved by shaking at 1400 rpm in a heating block at 95° C. for 5 min, and centrifuged at 4000 rpm for 2 min.

For the hydrolysis, 50 µl of the approx. 5% strength inulin solution are put into the digestion mix consisting of 50 µl of 1M Na citrate pH 4.6, 25 µl of exo-inulinase (Megazyme International Ireland Ltd, Wicklow, Ireland, article No. E-EXO1, 2.5 U/µl) and 375 µl of dd $H_2O$. The digestion is mixed and centrifuged at 4000 rpm for 1 min. The digestion is then incubated on a heating block at 40° C. for 4 h. All digested samples are frozen at −20° C. Before the sugar measurement, these samples are thawed at room temperature, mixed and centrifuged at 4000 rpm for 2 min. For the fructose measurement, a 1:10 dilution is prepared by adding 10 µl of digestion to 90 µl of dd $H_2O$.

To determine the fructose and glucose liberated in the digestion, a photometric measurement of glucose and fructose is carried out in all the samples as described under "sugar determination (glucose, fructose, sucrose)". Besides glucose and fructose, also sucrose is determined in the sample before the digestion.

The undiluted 5% strength inulin solution is used for sugar measurement before the digestion. 10 µl of this solution are added to 200 µl of measurement buffer. For glucose measurement in the digested samples, 10 µl of the undiluted samples are added to 200 µl of measurement buffer. For fructose measurement in the digested samples, 10 µl of samples diluted 1:10 are added to 200 µl of measurement buffer.

The calculation is based, as in the sugar determination, on a molar extinction coefficient of 6.23 $l*mmol^{-1}*cm^{-1}$ for the conversion of NADP to NADPH. The concentration of glucose and fructose present before the digestion is subtracted from the glucose and fructose concentrations in the digested samples. Likewise, the glucose and fructose which would be liberated from hydrolyzed sucrose present in the sample before the digestion is subtracted.

The concentrations of fructose and glucose formed during the digestion of inulin are then obtained. The fructan content is obtained by addition of the glucose and fructose contents and with inclusion of the factor 162/180 for conversion of the measured free hexoses into the hexoses bound in the fructan.

2. Sugar Determination (Glucose, Fructose and Sucrose)

The glucose, fructose and sucrose contents were determined by photometry in an enzymatic assay via conversion of $NADP^+$ (nicotinamide adenine dinucleotide phosphate) to NADPH (reduced nicotinamide adenine dinucleotide). The aromatic character of the nicotinamide ring is lost in the reduction, and thus the absorption spectrum is changed. This change in the absorption spectrum can be detected by photometry.

Glucose and fructose are converted by means of the enzyme hexokinase and adenosine triphosphate (ATP) into glucose 6-phosphate and fructose 6-phosphate. The glucose 6-phosphate is then oxidized by the enzyme glucose-6-phosphate dehydrogenase to 6-phosphogluconate. $NADP^+$ is reduced to NADPH in this reaction, and the amount of NADPH formed is measured by photometry. The ratio of NADPH formed to the glucose present in the extract is 1:1, so that the glucose content can be calculated from the NADPH content using the molar extinction coefficient of NADPH (6.23 l mmol$^{-1}$ cm$^{-1}$) according to Lambert-Beer's law.

After the oxidation of the glucose 6-phosphate is complete, the fructose 6-phosphate which is likewise produced in the solution is converted by the enzyme phosphoglucoisomerase into glucose 6-phosphate, which in turn is oxidized to 6-phosphogluconate. The ratio of fructose and the amount of NADPH formed is also 1:1. The fructose content is calculated from the amount of NADPH formed, as described for glucose.

Subsequently, the sucrose present in the extract is cleaved by the enzyme sucrase (from Megazyme) into glucose and fructose. The liberated glucose and fructose molecules are then converted by the abovementioned enzymes in the NADP$^+$-dependent reaction into 6-phosphogluconate. Two molecules of NADPH are formed in the conversion of one molecule of sucrose into 6-phosphogluconate. The amount of NADPH formed is likewise measured by photometry, and the sucrose content is calculated therefrom using the molar extinction coefficient of NADPH.

A 5% strength inulin solution as described under "Fructan determination by hydrolysis with exo-inulinase" is used for the sugar measurement. 10 μl of this solution are added to 200 μl of measurement buffer. The measurement takes place as duplicate determination in microtiter plates using the SPECTRAmax photometers (Molecular Devices). All the enzyme solutions used are made up in measurement buffer consisting of 50 mM imidazole HCl pH 6.9, 2.5 mM MgCl$_2$, 1 mM ATP and 0.4 mM NADP. The conversion of NADP to NADPH is followed at a wavelength of 340 nm.

The glucose determination takes place by adding 2 μl of a mix of hexokinase (from yeast, 0.3 U/μl) and glucose-6-phosphate dehydrogenase (from yeast, 0.14 U/μl). After conversion of the glucose is complete, 2 μl of phosphoglucose isomerase (from yeast, 0.14 U/μl) are added to determine fructose. When the fructose is completely converted, 2 μl of sucrase (from Megazyme, 0.2 U/μl) are added to cleave the sucrose present. The calculation of glucose, fructose and sucrose takes place as described.

3. Analysis of the Molecular Weight Distribution
3.1 Gel Permeation Chromatography with Light Scattering and Refractive Index Detection (GPC-RI-Malls System)

The inulins/fructans are dissolved in extra-pure water in a concentration of 0.5% (w/v). The solutions are heated at 95° C. for 30 minutes. The polymers are analyzed using the following devices: Alliance chromatography system (Waters corporation, Milford, Mass., USA), DAWN-EOS light scattering detector (Wyatt Technology, Santa Barbara, USA) with $\lambda_0$=658 nm and 16 detectors in the range of angles from 14.4 to 163.3°, K5 flow cell. The polymers are fractionated on a precolumn and three columns having the separation ranges 300-10$^4$, 5×10$^4$–2×10$^6$ and 10$^6$-10$^8$ (SUPREMA-Gel, PSS Polymer Standards Service GmbH, Mainz, Germany). 100 μl of solution are injected. The fractionation takes place at a temperature of 30° C. and a flow rate of 0.8 ml/min with 0.05M NaNO$_3$ as eluent. The Astra V 5.1.8.0 program (from Wyatt Technology, Santa Barbara, USA) is used to analyze the molecular weight distribution of the samples.

3.2 Gel Permeation Chromatography with Refractive Index Detection (GPC-RI system)

The inulins are dissolved in the eluent (DMSO+90 mM NaNO$_3$) in a concentration of 1% (w/v) by shaking gently in a thermal shaker at 95° C. for 10 minutes. After brief cooling, the inulin solution is diluted to 0.1% with eluent (100 μl of inulin solution+900 μl of eluent) and immediately placed in the autosampler at 60° C. The polymers are analyzed using the following apparatus: Dionex P580 pump, Dionex AS50 autosampler, Dionex model 585 column oven (Dionex GmbH, Idstein, Germany), Shodex RI-71 detector (Shodex/Shoko Co. LTD, Tokyo, Japan). The systems are controlled by the Chromeleon software (Dionex GmbH, Idstein, Germany). The polymers are fractionated on a PSS GRAM, 10μ, precolumn and the PSS GRAM 3000, 10μ and PSS GRAM 100, 10μ separation columns (PSS Polymer Standards Service GmbH, Mainz, Germany). 50 μl of the 0.1% inulin solution are injected for the analysis. The fractionation takes place in the column oven at a temperature of 60° C. and with a flow rate of 0.7 ml/min with the eluent DMSO+90 mM NaNO$_3$. To determine the molecular masses, the system is calibrated with the following dextran standards (product No. 31430, Fluka Riedel-deHaen, Seelze, Germany): dextran T1 (Mw 1270), T5 (Mw 5220), T12 (Mw 11 600), T25 Mw 23 800), T50 (Mw 48 600), T80 (Mw 80 900), T150 (Mw 147 600), T270 (Mw 273 000), T410 (Mw 409 800) T670 (667 800). The PSS WinGPC compact V.6.20 program (PSS, Mainz, Germany) is used to analyze the molecular weight distribution of the samples.

4. Determination of the Water Content

The water content is determined using an AQUA 40.00 Karl-Fischer titrator (from analytikjena AG). Hydranal-Coulomat AG (Riedel-deHaën, article No. 34 836) is used as anolyte. The reference substance used is dibasic sodium tartrate dihydrate (Riedel-deHaën, article No. 32 323) with a moisture content of 15.61-15.71%. 10-20 mg of sample are weighed into 5 ml sample bottles (N20-5DIN, Machery-Nagel, article No. 702 04.36), the bottles are closed with crimped caps (N20 TS/oA, Machery-Nagel, article No. 702 815), and the water content of the sample is determined using the Karl-Fischer titrator.

5. Determination of the Degree of Branching

The inulins are initially permethylated and the completeness of the methylation is checked by ATR-IR spectroscopy (see below for apparatus and conditions). The samples were then decomposed by acidic hydrolysis (standard methylation analysis) or alternatively by reductive degradation into their monomer building blocks, and the relative molar composition was determined by gas chromatography (see below for apparatus and conditions) and gas chromatography mass spectroscopy (GC-MS, see below for apparatus and conditions) of the partially methylated alditol acetates and anhydroalditol acetates.

| ATR-IR | |
|---|---|
| Apparatus: | Bruker Tensor 27 |
| Technique: | Diamond ATR |

| GC: | |
|---|---|
| Apparatus: | Carlo Erba HRGC 5160 Mega Series |
| Column: | Chrompack CPSil8CB (25 m) with retention gap (1.5 m) ID: 0.25 mm FD: 0.25 μm |
| Carrier gas: | He (80 kPa) |
| Detector: | FID |
| Injector: | on column |
| Integrator: | Merck Hitachi D-2500 Chromato-Integrator |
| Temperature program: | 60° C. (1 min isothermal), 10° C./min to 170° C., 3° C./min to 230° C., 20° C./min to 290° C. (20 min isothermal) |

| GC-MS | | |
|---|---|---|
| GC: | Apparatus: | Agilent 6890 GC |
| | Column: | HP-5, 30 m |
| | Carrier gas: | He |
| | Injector: | Split 5:1 |
| | Temp. program: | 60° C. (1 min isothermal), 10° C./min to 170° C., 3° C./min to 230° C., 20° C./min to 290° C. (20 min isothermal) |
| MS: | Apparatus: | JEOL GCmate II double-focusing sector field spectrometer |
| | Mode: | EI, 70 eV |
| | Evaluation: | AMDIS32, Wsearch32 |

5.1 Permethylation (according to Ciucanu and Kerek/Ciucanu, I. & Kerek, F. (1984) A simple and rapid method for the permethylation of carbohydrates. Carbohydr. Res. 131, 209-217.)

About 50 mg of sample are dissolved in 2.5 ml of dimethyl sulfoxide. Then 3 eq/OH of finely ground sodium hydroxide and 3 eq/OH of methyl iodide are added and stirred at room temperature for 24 hours. Then half the amount of each of the reagents is added once again. The samples are subsequently dialyzed against distilled water for four days (dialysis membrane Spectra/Por MWCO 3500, Spectrum Laboratories, Rancho Dominguez, Calif., USA) and freeze dried. The completeness of the methylation is checked by ATR-IR spectroscopy. The OH stretching vibration in the range 3300-3400 cm$^{-1}$ should have disappeared if there is pemethylation.

5.2 Standard Methylation Analysis

Hydrolysis

About 2 mg of permethylated inulin are mixed in a 1 ml V vial with 0.9 ml of 0.5 M trifluoroacetic acid and hydrolyzed by stirring at 90° C. for one hour. After the solution has cooled it is evaporated to dryness in a stream of nitrogen. Trifluoroacetic acid residues are removed by codistillation with toluene.

Reduction

The hydrolyzed sample is mixed with 500 µl of a 0.5 M NaBD$_4$ solution in 2 M NH$_3$ and heated at 60° C. for one hour. After cooling, excess sodium borohydrite is decomposed by adding a few drops of glacial acetic acid. Resulting borate is removed by codistillation with 15% strength methanolic acetic acid.

Acetylation

The partially methylated sugar alcohols resulting from the reduction are mixed with 200 µl of acetic anhydride and 50 µl of pyridine and acetylated at 90° C. for 2 hours. The solution is cooled and then saturated sodium bicarbonate solution is added until no further gas formation is to be observed. It is then extracted four times with 15 ml of dichloromethane each time. The combined organic phases are washed twice with 15 ml of saturated NaHCO$_3$ solution each time, once with 20 ml of cold 0.1 M HCl and once with 25 ml of distilled water. The solution is then dried over calcium chloride and concentrated in vacuo, and taken up in dichloromethane for the GC measurement.

5.3 Reductive Degradation

About 1 mg of the permethylated sample is dissolved in 500 µl of dichloromethane in a screw-cap glass vial, mixed with 6 eq/glycoside bond on triethylsilane and 4 eq of TMS triflate and stirred at room temperature for 2 hours. After addition of 20 µl of acetic anhydride, stirring is continued at room temperature for 2 hours. The reaction is then stopped by adding saturated aqueous NaHCO$_3$ solution, and stirring is continued for 1 hour. Working up takes place by extraction with dichloromethane and subsequent washing of the combined organic phases with saturated aqueous NaHCO$_3$ solution and distilled water. The solution is finally dried over calcium chloride, concentrated in a stream of nitrogen and taken up in dichloromethane for the GC measurement.

5.4 Qualitative and Quantitative Analysis

The degradation products were analyzed quantitatively by gas chromatography with on-column injection and flame ionization detector (FID). The peak areas were corrected according to their effective carbon response. The peaks were assigned on the basis of their mass spectrum (GC-MS) and the retention times of known comparison samples.

6. Differential Scanning Calorimetry of Inulin 40 ml of a 15% strength (w/v) inulin solution were prepared in 50 ml graduated polypropylene tubes (30.0×115 mm, from Greiner, order number 227261). This was done by adding the respective powder to double-distilled water and shaking. Subsequently, all the prepared suspensions are placed in a waterbath (95° C.) and dissolved by shaking several times. After 20 minutes, it is established visually that all the suspensions have completely dissolved. The prepared solutions are then divided in equal parts to two 50 ml graduated polypropylene tubes (30.0×115 mm, from Greiner, order number 227261) and immediately deep frozen in liquid nitrogen. The frozen solutions were then freeze dried for two days (water content about 10%) and ground in a mortar.

The water content of the samples is determined using an automatic Karl-Fischer titrator (see general methods 4).

For a DSC measurement, about 10 mg of inulin dry substance are weighed into a stainless steel crucible (volume 50 µl), the exact weight is found, and 30 µl of distilled water are added. The crucibles are then hermetically sealed. An empty stainless steel crucible is used as reference. The sample is heated in a DSC apparatus with autosampler (Perkin Elmer; Diamond) from 10-160° C. at a heating rate of 10° C./minutes. The data analysis is carried out by the PYRIS 7.0 software program (Perkin Elmer, 63110 Rodgau-Jügesheim, Germany). This entailed determination of To (onset) and the free enthalpy dH.

7. Viscosity Determination

Aqueous inulin solutions of various concentrations (weight per volume of distilled water) were prepared by shaking at 98° C., and the clear solutions were measured immediately after a dissolving time not exceeding 13 min. The measurements were carried out in a BOHLIN Gemini Advanced Rheometer (Malvern Instruments; Herrenberg, Germany) using the isothermal (90° C.) viscometry mode on a CP4°/40 mm cone-plate system. The measuring gap was covered with a layer of extra light paraffin oil. A shear rate of 10 s$^{-1}$ for 60 s with a 10 s relaxation time was used for preshearing. The shearing was measured in logarithmic steps in a shear rate mode. The initial shear rate was 20 s$^{-1}$, the final shear rate was 30 s$^{-1}$ in an increasing ramp with a holdup time of 20 s an an integration time of 10 s. The data are based on the average values in the range from 20 s$^{-1}$ to 30 s$^{-1}$ and are the means of three independent measurements per data point. All measurements specified as outliers are not included in the average values. The definition of "outlier" took place by the so-called "quartile method". This entailed outliers being specified as all measurements lying outside the range criterion $Q_2-k*(Q_3-Q_1) \leq$ no outlier $\leq Q_2-k*(Q_3-Q_1)$ (SACHS, Lothar: Angewandte Statistik, 10th edition, Springer-Verlag Berlin (2002), pp. 364 et seq.). $Q_1$ and $Q_3$ here is the 25% quartile and the 75% quartile, respectively, and $Q_2$ is the median (50% quartile) of the measured data. A value of 1.5 was used for the factor k.

8. Determination of Gel Strength and Viscoelastic Behavior 70 g of a 17% by weight suspension of inulin in water (distilled) was put into an MV measuring cup of a Haake Rotovisco VT 550 viscometer. A paddle stirrer was then inserted and mounted in the preheated (90° C., heating jacket) apparatus. The mixture was then heated with stirring at 128 rpm for 15 min.

After 15 min, the mixture was transferred at 90° C. into a container which consisted of a base and a wall composed of two cylindrical rings of acrylic sheet (each 20 mm high, 30 mm diameter) which were placed one on top of the other and were fastened together by means of an adhesive tape (19 mm wide). The mixture was introduced into the container without bubbles until the level was about 5 mm below the upper edge. The container was then hermetically covered with an aluminum foil and left to stand at room temperature (23° C.) overnight.

The gel strength was measured after storage at room temperature (23° C.) for about 20 hours using a TA XT2 texture analyzer. To make measurement of the gel strength possible on a smooth, undried surface, firstly the adhesive tape which held the two cylindrical rings of the container together was removed. The gel was then divided with a razorblade between the rings so that the lower part of the gel exhibited a smooth surface.

The gel strength was measured with the TA XT2 texture analyzer by a level dome (diameter 24.5 mm) penetrating (1 mm) into the gel. The settings on the texture analyzer were as follows:

| Measurement principle: | force in direction of pressure |
|---|---|
| Forward speed: | 2 mm/s |
| Test speed: | 2 mm/s |
| Trigger value: | 0.01 N |
| Reverse speed: | 2 mm/s |
| Travel: | 1 mm |

The maximum value with a single penetration of the dome in newtons is indicated.

Example 1

Characterization of the Inulin from Artichoke Roots

1. Cultivation of the Artichoke Plants

The artichoke plants of the Madrigal variety were grown in the vicinity of Valencia, Spain. The seeds were sown in April 2005, and the plants were harvested in August/September 2005. The roots were separated from the above-ground part, freed of adherent soil and dried. The roots were then transported without cooling from Spain to Germany. The roots were stored at −20° C. until the inulin was extracted.

2. Inulin Preparation from Artichoke Roots

Roots from artichoke plants of the Madrigal variety about 4-5 months old are used to prepare the inulin. 60 kg of roots are freed of the soil constituents adhering to them by washing in the deep-frozen stage with a high-pressure cleaner (Kärcher, Winnenden, type HD 700) before they are further processed to chips in a shredder (Gloria Universal garden shredder natura 2800L). The chips are put into a jacket-heated extracter with gate agitator containing water preheated to 70-90° C. The total amount of water added is 180 kg. The pH of the extract is adjusted to 9.0 by adding NaOH. After rapid heating of the chip mash to 80-85° C. via the jacket of the extractor, the mash is agitated at 80-85° C. for about 60 min in order to extract the inulin (fructan) from the chips. After this time, crude extract is separated from the chips by pumping off.

The crude extract is decolorized in a two-stage process by forming a total of 0.7 g of $Mg(OH_2)/100$ ml of extract. In the first stage, 3400 g of $MgSO_4 \cdot 7H_2O$ (equivalent to 0.5 g of $Mg(OH_2)/100$ ml of extract) are dissolved in 170 L of dark-brown colored extract with stirring over the course of 10 min. Subsequently, 1015 g of 96% strength $Ca(OH)_2$ are added as suspension in 3 L of water and stirred for 10 min. A pH of 9.4 is set up. The whole precipitation mixture is quantitatively clarified in a plate separator (GEA, Westfalia type SC 6-06-076) over the course of 120 min. The decolorized extraction solution has a pale yellow color and is free of materials causing turbidity. A solid phase in the form of a thick paste is obtained as removed sludge fraction. The entire decolorization step is repeated on the extraction solution obtained in this way and comprising 150 L with $MgSO_4 \cdot 7H_2O$ (equivalent to 0.2 g $Mg(OH_2)/100$ ml of extract) and 410 g of 96% strength $Ca(OH)_2$ as suspension in 1.5 L of water. The whole precipitation mixture is quantitatively clarified in a plate separator over the course of 30 min. The decolorized extraction solution with a pH of 9.4 is clear, has a pale yellow color and is free of materials causing turbidity. A centrifugate of 7 l in the form of a thick paste is again obtained as sludge fraction.

Solid inulin is obtained from the extract brightened in this way by cooling at a temperature of 4° C. over a period of 48 h. The inulin is obtained as sludge-like sediment by centrifugal deposition using the plate separator.

The sediment is further purified twice in succession in the same concentration as present in the brightened extract by dissolving the inulin in hot water and renewed precipitation by storage at 2° C. for 48 h. The inulin sediment obtained after the second precipitation is freeze dried.

FIG. 1 shows a diagrammatic representation of the progress of the extraction.

Figure 2:
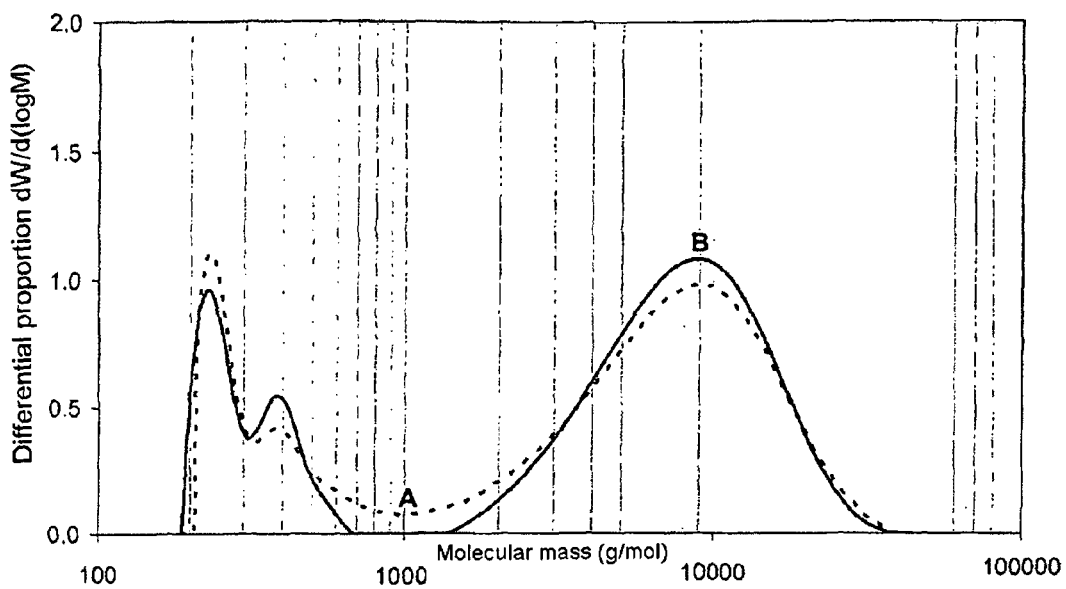
FIG. 2 shows a GPC-RI analysis of the polymer distribution in washed artichoke roots (A) and the extract after the hot water extraction inulin (B).

During the extraction process, the polymer distribution was analyzed after the individual extraction and purification steps by gel permeation chromatography with refactor index detection and calibration with dextran standards (GPC-RI system, see Method 3.2 in "General Methods"). As evident from FIG. 2, the polymer distribution of extract (B) after the hot-water extraction is comparable to that in the washed roots (A). FIG. 2 shows a GPC-RI analysis of the polymer distribution in the washed artichoke roots (A) and the extract after the hot-water extraction of inulin (B).

Figure 3:
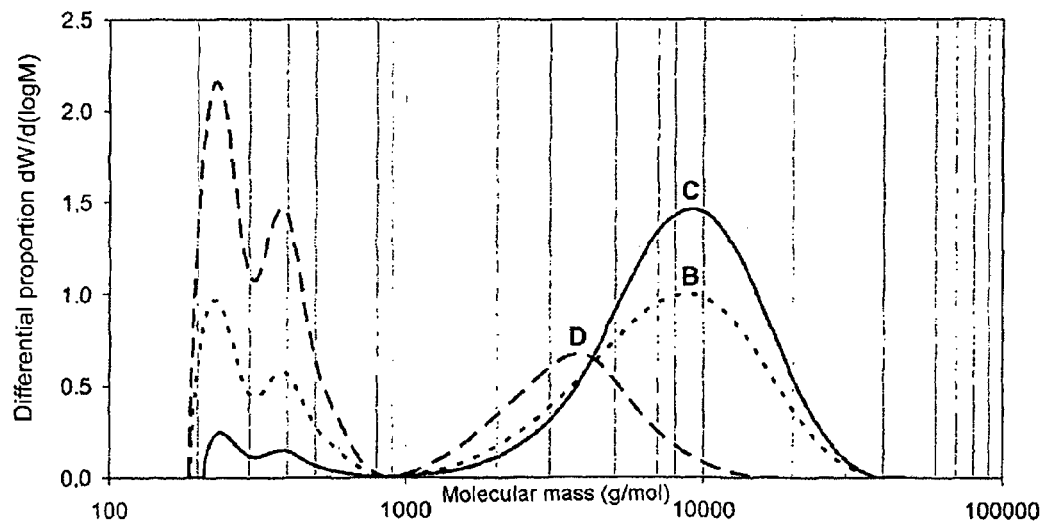
FIG. 3 shows a GPC-RI analysis of the polymer distribution in the extract after the hot-water extraction of the inulin (B), in the sediment after the inulin precipitation at 4° C. (C) and in the upper run obtained after centrifugation of the inulin after precipitation (D).

Analysis of the polymer distribution after the cold (4° C.) precipitation of the inulin showed that a high molecular weight inulin fraction (C) was separated from a low molecular weight fraction (D) (FIG. 3). FIG. 3 shows a GPC-RI analysis of the polymer distribution in the extract after the hot-water extraction of inulin (B), in the sediment after the inulin precipitation at 4° C. (C) and in the upper run obtained after centrifugation of the inulin after precipitation (D).

Figure 4:
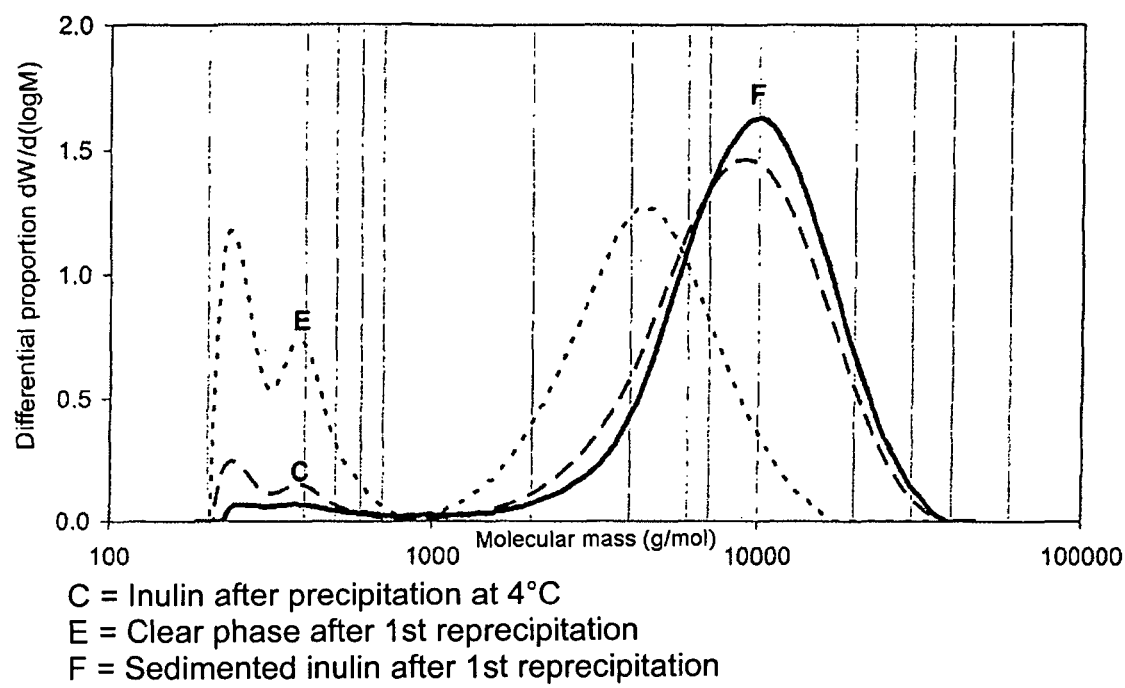
FIG. 4: GPC-RI analysis for the polymer distribution in the inulin precipitated at 4° C. (C), in the sediment after the reprecipitation (F) and in clear phase after the reprecipitation (E).

A further enrichment of high molecular weight inulin and a depletion of low molecular weight substances, especially mono- and disaccharides, were achieved by reprecipitation of the high molecular weight inulin fraction (FIG. 4). FIG. 4: GPC-RI analysis of the polymer distribution in the inulin precipitated at 4° C. (C), in the sediment after the reprecipitation (F) and in clear phase after the reprecipitation (E).

3. Determination of the Purity of the Prepared Inulin

The purity of the prepared artichoke inulin obtained in section 2 was determined by determining the fructan and water contents of the freeze-dried material. The water content determined for the artichoke inulin was 1.7% (see method "Determination of the water content").

The fructan content was determined by hydrolyzing the inulin with the enzyme exo-inulinase (see method "Fructan determination by hydrolysis with exoinulinase"). The purity based on dry matter (DM) was found from the fructan content and the water content. Purity=fructan content×100/(100−water content)

As is evident from Table 1, the average degree of purity of the prepared artichoke inulin is 97% of the dry matter (DM).

TABLE 1

Determination of the purity of the prepared artichoke inulin

| Material | Water content [%] | Exo-inulinase digestion Fructan [% of initial weight] | Purity [% TM] |
|---|---|---|---|
| Artichoke inulin | 1.7 | 95 ± 3 | 97 |

Figure 5:
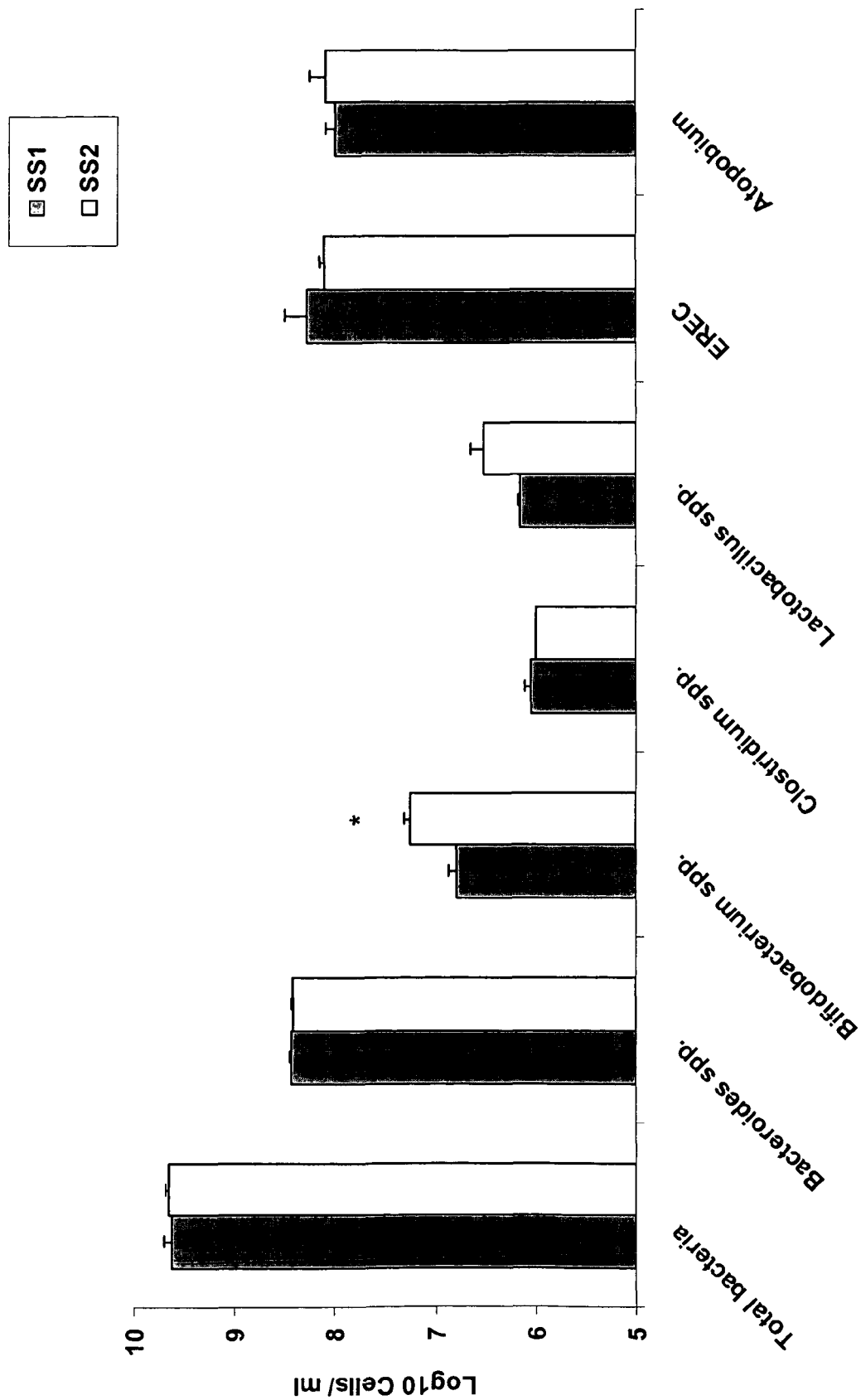
FIG. 5 shows the comparison of the bacterial population in vessel 1 (V1) between steady state 1 (SS1) and steady state 2 (SS2) after treatment with inulin of the invention.

4. Molecular Weight Determination by GPC-RI-MALLS 0.5% (w/v) aqueous solutions were prepared from the purified artichoke inulin obtained in section 2, and from purchased reference samples of Raftiline HP (from Orafti, batch: HPBNH4DNH4) and inulin from dahlia tubers (from Sigma, article number 1-3754, batch: 75H7065), and the molecular mass distribution of the inulins was determined by gel permeation chromatography (see method 3.1). This distribution is depicted in FIG. 5, and the molecular masses (anhydrofructose=162 g/mol) and average chain lengths calculated therefrom have been summarized in Table 2.

Analysis of the molecular weight distribution using the GPC-RI-MALLS system resulted in a weight average molecular mass Mw of 12 088 g/mol and a number average molecular mass Mn of 11 500 g/mol for the artichoke inulin. This corresponds to an average chain length of 75 for DPw and of 71 for DPn. The chain lengths of the purified artichoke inulin are on average distinctly longer than those of Raftiline HP (DPw=33, DPn=29) and of dahlia inulin (DPw=39, DPn=33). This is also reflected in the minimum and maximum molecular masses, which are distinctly larger for artichoke inulin.

TABLE 2

Molecular mass distribution of various inulins

| Material | $M_w$ [g/mol] | $M_n$ [g/mol] | Polymer distribution (min-max) [g/mol] | DPw | DPn | Molecular dispersity |
|---|---|---|---|---|---|---|
| Artichoke inulin | 12 088 | 11 500 | 4385-26 086 | 75 | 71 | 1.06 |
| Raftiline HP | 5391 | 4738 | 999-15 162 | 33 | 29 | 1.14 |
| Dahlia inulin | 6250 | 5407 | 1139-19 569 | 39 | 33 | 1.18 |

5. Results of Glucose, Fructose and Sucrose Determination

The proportion of glucose, fructose and sucrose in the artichoke inulin obtained in section 2 was determined by photometric determination of the sugars in 5% strength inulin solutions as described in Method 3 ("Sugar determination").

As is evident from Table 3, the glucose and sucrose contents in the purified artichoke inulin are less than 0.1% of the inulin powder, the fructose content is 0.12% of the inulin powder.

TABLE 3

Content of glucose, fructose and sucrose in purified artichoke inulin

| Material | Glucose (g/100 g inulin powder) | Fructose (g/100 g inulin powder) | Sucrose (g/100 g inulin powder) |
|---|---|---|---|
| Artichoke inulin | <0.1 | 0.12 | <0.1 |

6. Degree of Branching 6.1 Standard Methylation Analysis

The degree of branching was measured in an inulin sample of the invention having a DPw of 75 and a DPn of 71 and a spread of 1256-31 631 g/mol. The comparative examples used were Raftiline HP (from Orafti, batches HPBNO3DNO3 and HPBNH4DNH4) and inulins from dahlia tubers (from Sigma, article number I-3754, batch: 022K7045 or 75H7065) and Jerusalem artichoke roots (Sigma, article number I-2880 batches 111H7045 and 88F7220) the degree of branching were determined by means of methylation analysis (see General Methods, 5.1).

Hydrolysis, reduction and acetylation of 2-1-linked fructans result in 1,2,5-tri-O-acetyl-3,4,6-tri-O-methyl-D-mannitol and -sorbitol. The terminal fructosyl radicals afford 2,5-di-O-acetyl-1,3,4,6-tetra-O-methyl-D-mannitol and -sorbitol. A terminal glucopyranosyl unit results in 1,5-di-O-acetyl-2,3,4,6-tetra-O-methyl-D-sorbitol. Building blocks additionally branched in position 6 give the corresponding 1,2,5,6-tetra-O-acetyl-3,4-di-O-methylalditols.

Besides the products indicating 2-1 linkage, it was possible to detect in all fructan samples those from terminal fructose and glucose building blocks. The chromatograms additionally showed difructose dianhydride (DFDA, approx. 3 mol %) which is formed on removal of TFA in a stream of nitrogen from 2-1 linked fructose.

From the mass spectra it was additionally possible to identify products resulting from a 2-1,6 linkage in all the samples. 1,3- and 1,4-acetylated compounds were also identified, which would arise with branches in positions 3 and 4, respectively, but may also derive from incomplete methylation. The nonspecific occurrence of 1,3- and 1,4-acetylated products is an indicator of submethylation. Assuming that position 6 is affected by submethylation to the same extent as positions 3 and 4, the nonspecific proportion (average of 1,3-Ac and 1,4-Ac compounds) is subtracted from the proportion of 2-1, 6-branched fructose units. Table 4 below shows the results resulting therefrom.

TABLE 4

| Sample | | 2-1,6-Fructose [mol %]* |
|---|---|---|
| Inulin | Artichoke | 1.1** |
| | RaftilineHP | 0.4 |
| | Dahlia | 0.2 |
| | Jerusalem artichoke | not detected |

*based on all species found
**average of two measurements

Evaluation of the methylation analysis revealed a degree of branching of 1.1 mol % for the artichoke inulin. The degree of branching of this inulin is thus distinctly higher than that in the inulins of the reference samples from chicory (RaftilineHP), dahlia and Jerusalem artichoke.

Example 2

Properties of the Inulin from Artichoke Roots

All the following investigations relate to the artichoke inulin of the invention described previously in Example 1 and detailed previously in Tables 1-4. The comparative Raftiline HP and dahlia inulins are likewise those detailed in Example 1.

1. Differential Scanning Calorimetry Investigation of Inulin

The differential scanning calorimetric analysis of inulin (for procedure: see methods) showed distinct differences between the various materials (see Table 5 below) in relation to the melting behavior. Both inulin samples differed greatly in relation to the enthalpy of fusion. This was above 29 J/g for artichoke inulin and only 22.8 J/g for Raftiline HP. The differences in $T_{onset}$ (To) were somewhat less, but the initial melting temperature for artichoke inulin was 40.4° C. which was more than 2.5° C. higher than for the comparative chicory inulin. This increased thermal stability of artichoke inulin may be a considerable advantage in certain thermal processes in the food products sector, because the artichoke inulin is distinctly less sensitive to high temperatures than chicory inulin.

TABLE 5

| Material | To [° C.] | Enthalpy of fusion dH [J/g] |
|---|---|---|
| Artichoke inulin | 40.4 | 29.1 |
| Raftiline HP | 37.8 | 22.8 |

2. Viscosity

TABLE 6

Comparison of the dynamic viscosity of chicory inulin and artichoke inulin in water as a function of the concentration (T = 90° C.)

| Concentration | Viscosity (mPas) | |
|---|---|---|
| % (w/v) | Raftiline HP (chicory) | Artichoke inulin |
| 10 | 2.4 | 2.3 |
| 24 | 4.3 | 5.4 |
| 26 | 4.2 | 12.2 |
| 28 | 4.5 | 15.7 |

As is evident from the above table, both inulins showed at concentrations of up to 24% (w/v) very low viscosities at 90° C. (water=1 mPas). The inulin of the invention became viscous at concentrations of 26% (w/v) and especially at 28%, whereas Raftiline HP remained very similar in its viscosity to water up to 28% (w/v).

3. Particle Size after Freeze Drying

The freeze-dried sample from example 1 was ground in a knife mill (Grindomix GM200, Retsch Technologie GmbH, Haan, Germany) and the particle size was determined by sieve analysis (vibrating sieve machine "Analysette 3" from Fritsch, frequency 2.0, sieving aids: 8 agate balls (10 mm Ø)/sieve, sieving time 1-2 min, amount loaded about 50 g). The result is shown in table 7 below. It was possible to determine the average particle diameter by sieve analysis as 126 μm.

TABLE 7

| Mesh width/μm | Mass/g | % |
|---|---|---|
| <63 | 12.80 | 25.78 |
| <90 | 4.99 | 10.05 |
| <125 | 6.60 | 13.29 |
| <160 | 6.26 | 12.61 |
| <200 | 5.09 | 10.25 |
| <500 | 13.75 | 27.69 |
| >500 | 0.16 | 0.32 |
| Total | 49.65 | 100.00 |

4. Spray Drying, Particle Size

An inulin with DPw=81 was prepared as described in example 1. After an intermediate freeze drying, it was redissolved and then spray dried on a Glatt GPCG3.1 fluidized bed spray-drying unit. For this purpose, freeze-dried inulin was introduced into water, heated to 85-90° C. and dissolved. The heated solution was spray dried with varying outlet air temperature, and the process properties and product properties were observed. The inlet temperature was kept constant at 120° C. The feed consisted of 80% water and 20% inulin, the feed temperature was 85-90° C. and the outlet air temperature was 80° C.

The particle size distribution was determined by sieve analysis as described above. The results of the sieve analysis of the spray-dried sample are indicated in table 8 below. The average particle size of the spray-dried product was determined from the particle size distribution of the sieve analysis to be <60 μm.

TABLE 8

| Mesh width/μm | Mass/g | % |
|---|---|---|
| <63 | 34.63 | 69.9 |
| <90 | 9.43 | 19.0 |
| <125 | 3.03 | 6.1 |
| <160 | 1.05 | 2.1 |
| <200 | 0.53 | 1.1 |
| <500 | 0.86 | 1.7 |
| >500 | 0.00 | 0.0 |
| Total | 49.53 | 100.00 |

5. Crystallinity

Inulin samples in powder form were prepared without further pretreatment in a 2 mm-thick sample carrier (standard) between two PET covering films. The X-ray measurements were carried out with a D5000 two-circle diffractometer from Bruker-AXS in symmetrical transmission using monochromatic (Ge(111) monochromator) Cu—Kα radiation. The recordings were made at 30 mA and 40 kV in the 2θ angle range of 3-29° (step width Δ2θ=0.1°) and 29.5-104 (step width Δ2θ=0.5), step/Δ2θ: 60 seconds.

Software based on the Ruland-Vonk method (WAXS 7, developed by the Fraunhofer Instituts für angewandte Polymerforschung, Potsdam (DE), described in http://edocs.tu-berlin.de/diss/2003/rihm_rainer.pdf, pp. 19 et seq.) was used to find the degree of crystallinity $x_c$, the crystallite sizes $D_{(hkl)}$ and the disorder parameter k, which is a measure of the disturbance of the lattice in the crystallites, from the scattering plots. The scattering plot for sample 2 (see below) was used as amorphous background file. Fructose was used as chemical basis, calculated with a density of 1.65 g/cm³. The crystallite sizes $D_{(hkl)}$ were determined from the half-widths of the X-ray reflections by the Scherrer formula at the first two main interferences at 2θ=8° and 12°.

The sample of a freeze-dried inulin with a DPw of 77-82 and of a drum-dried inulin with DPw 81 was measured. The results obtained are in table 9 below:

TABLE 9

|  | Crystallinity $x_c$ [%] | Disorder parameter k [$10^{-2}$ nm$^2$] | D(hkl) 2θ = 8° [nm] | $D_{(hkl)}$ 2θ = 12° [nm] |
|---|---|---|---|---|
| Inulin freeze dried | 35 | 4.9 | 5.7 | 7.3 |
| Inulin drum dried | 28 | 2.4 | 6.7 | 10.1 |

6. Structure Formation of the Inulins after Heating in Water 15 ml portions of 20% strength suspensions of the inulins in water were each made up in aluminum beakers (RVA-3d beakers from Winopal Forschungsbedarf GmbH; volume about 70 ml, diameter 38 mm), stirred up and equipped with a magnetic stirring bar and finally covered. The suspensions were heated using a multithermal stirrer (VARIOMAG Multitherm 15 from H+ P Labortechnik AG) with stirring. The temperature was controlled in this case by using a PT 100 probe (accessory for the VARIOMAG Multitherm 15) which stood in a covered reference beaker with distilled water on the heating block. The multithermal stirrer was preheated so that the temperature of the reference sample remained stable at 90° C. The suspensions to be heated were placed on the multithermal stirrer and stirred at 90° C. for 8 min. The samples were then removed from the multithermal stirrer stored at room temperature for 24 hours. The strength of the resulting gels was then measured using a TA-TX2 texture analyzer (Stable Micro Systems). This measurement was carried out using the SMSP/0.5 R076 penetrating plunger (Stable Micro Systems) with a diameter of 12 mm as measurement system. The following parameters were applied for the TA measurement with the 5 kg measuring cell:

Options: measure force in direction of pressure
Single test
Parameter: forward speed 2.00 mm/s
Test speed 0.50 mm/s
Reverse speed 0.50 mm/s
Travel (depth of penetration) 3 mm
Trigger Force 2 g The structure-forming behavior of various inulins after thermal treatment in water was investigated. It emerged from this that the inulins from chicory (Raftiline HP® and Beneo HPX™) do not form gel-like structures under these conditions (table 10). In contrast thereto, the inulins from artichoke with DPw=77-81 or DPw=75 form very strong structures. Surprisingly, the sample in which the spray-dried inulin with DPw=81 was used also formed considerably stronger gels than the comparable samples (DPw=77-81 or DPw=75) in which the fructan was freeze dried. This is particularly clear from the fact that the gel strengths found with only 15% (w/w) concentration of inulin employed were at a similar level to those with the freeze-dried comparative samples at 20%.

TABLE 10

Structure formation of the fructans after heating in water

|  | Inulin concentration, % (w/w) | Gel strength [g] | Standard deviation |
|---|---|---|---|
| Raftiline HP ® DPw 33 | 20 | No gel | — |
| Beneo HPX ® DPw 33 | 20 | No gel | — |
| Inulin DPw 77-81 | 20 | 370 | 10* |
| Inulin DPw 75 | 20 | 350 | 44** |
| Inulin DPw 81, spray dried | 20 | 931 | 42* |
| Inulin DWw 81, spray dried | 15 | 289 | 69* |

*n = 2
**n = 4

7. Prebiotic Properties

The prebiotic effect of inulin according to the invention was investigated in an in vivo model study in a three-stage fermentation system (bowel model). The types of bacteria which colonize the fermentation system, and their metabolic activities (formation of short-chain fatty acids), were ascertained.

1. Materials and Methods:
a) Continuous Three-Stage Culture System:

A continuous three-stage culture system which has previously been described by Pereira et al. (2003) Appl Environ Microbiol 69(8), 4743-4752 and Probert et al. (2004) Appl Environ Microbiol 70, 4505-4511, was used in this study. The bowel model consisted of three culture vessels V1, V2 and V3 with working volumes of 0.28, 0.30 and 0.30 liters which were arranged in series. Each vessel was provided with a magnetic stirrer, the temperature was kept at 37° C. by means of a waterbath, and the pH in the individual vessels was controlled by an Electrolab pH controller. The entire system (including media reservoir) was operated under anaerobic conditions by passing sterile oxygen-free nitrogen through the liquid. The pH in the three vessels was adjusted by adding the appropriate amount of 0.5 M HCl-NaOH to 5.5 (V1), 6.2 (V2) and 6.8 (V3). Vessel 1 simulated the microbial conditions in the anterior large bowel. It was relatively rich in nutrients, had a relatively more acidic pH and a shorter residence time than vessel 3 with a more neutral pH and comparatively little substrate. Vessel 3 simulated the posterior part of the large bowel. Vessel 2 modeled the central, transverse part of the large bowel (transverse colon).

Oxygen-free nitrogen was continuously blown into the sterile culture medium, and it was introduced by means of a peristaltic pump into V1 which led sequentially to V2 and V3. The culture medium consisted of the following components in distilled water (g/L): potato starch, 5.0; pectin (citrus), 2.0; casein (sodium salt), 3.0; Raftiline LS (Orafti, Tienen; BE), 1.0; xylan (oat hull), 2.0; arabinogalactan (Fluka), 2.0; guargam, 1.0; mucin (porcine gastric type III), 4.0; tryptone (Oxoid), 5.0; peptone water (Oxoid), 5.0; yeast extract (Oxoid), 4.5; bile salts No. 3 (Oxoid), 0.4; L-cysteine HCl, 0.8; NaHCO3 (Fisher Scientific), 1.5; hemin, 0.05; NaCl (Fisher Scientific), 4.5; KCl (Fisher Scientific), 4.5; CaCl2×6H2O (BDH), 0.15; KH2PO4 (BDH), 0.5; FeSO4×7H2O (BDH), 0.005; MgSO4×7H2O (Fisher Scientific), 1.25. In addition, 1.0 ml of Tween 80 (BDH) and 10 microliters of vitamin K were added. A 4 ml concentration of a 0.025% (w/v) solution of resazurin was added to the growth medium as indicator of anaerobic conditions. The medium was autoclaved at 121° C. for 15 min and cooled under a nitrogen atmosphere. Unless indicated otherwise, all chemicals were purchased from Sigma Chemical Co., UK.

Collection and Preparation of Fecal Material:

The remaining volume of each vessel was made up with freshly prepared fecal suspension from a 30-year old man who had not taken any antibiotics for three months before the test. The 20% (w/w) fresh fecal suspension was prepared with previously reduced phosphate-buffered saline (PBS) and digested at normal speed for 2 minutes in a digestion apparatus (stomach). Large food residues were removed through a filter sack. One hundred ml of the resulting suspension were then employed to inoculate each of the three fermentation vessels. The system was initially operated as batch culture using the culture medium over 48 hours. After 48 h of batch culture fermentation, the complex growth medium which simulates the composition of intestinal fluid was introduced into V1 and then into V2 and V3 via the peristaltic pump. The residence time (R) was calculated as reciprocal dilution rate for each vessel. The residence time was set at 27.1 hours, and the system was operated for 12 days after the initial 48 h equilibrium period to ensure a steady state. The overall residence time was the total of the individual residence times R of each fermenter.

Sampling:

The first sample (5 ml) (day 0) was taken after fermentation for 24 h. The fermentation continued until a steady state was reached (after 10-12 days) (SS1). At this stage, samples of the culture liquid were removed from each vessel for subsequent analysis of bacteria and short-chain fatty acids, and used as indicator of SS1. After SS1 was reached, the test substrate was put into vessel 1 each day for a further period of 10-12 days. The fermentation was continued until a further steady state (SS2) was reached and once again samples were taken of the culture liquid from each vessel for subsequent analysis.

Counting of bacteria in fecal samples and samples from the bowel model by FISH analysis: Samples from individual vessels of the fermentation system were treated as shown below. Sample preparation: samples (375 µl) were removed from the batch cultures, added to 1125 µl of filtered 4% (w/v) paraformaldehyde solution (pH 7.2), mixed and stored at 4° C. overnight in order to fix the cells. The fixed cells were centrifuged at 13 000 rpm for 5 minutes and washed twice in filtered phosphate buffer solution and resuspended in 150 µl of PBS. Ethanol (150 µl) was added, and the sample was mixed and stored at −20° C. until used, but not for more than 3 months.

Hybridization:

The fixed cells (16 µl) were added to 264 µl of preheated (oven) filtered hybridization buffer (preheated in X (30 mM Tris-HCl, 1.36 M NaCl, pH 7.2, 0.1% v/v sodium dodecylsulfate, SDS) and mixed. The mixture was added to the suitable Cy3-labeled probe (50 ng/µl) in a ratio of 9:1 (v/v), mixed and placed in the hybridization oven at a suitable temperature overnight.

Washing and Filtering:

The hybridized sample (suitable aliquots to achieve from 30 to 150 cells per field of view) was added to 5 ml of preheated, filtered hybridization buffer (20 mM Tris-HCl, 0.9 M NaCl, pH 7.2) together with 20 µl of DAPI (4',6-diamidino-2-phenylindole, 500 ng/µl) and left at the suitable hybridization temperature for 30 min. The mixture was put on a black membrane filter with a pore size of 0.2 µm (GTBP 01300, Millipore Corp.). Slowfade-Light Antifade (Molecular Probes Europe, Leiden, NL) was put on the filter in order to prevent fading of the fluorescence, and the supports were stored in the dark at 4° C. for a maximum of 3 days.

A minimum of 15 fields of view per support was examined with a Nikon Microphot EPI fluorescence microscope (1000× magnification). The DM510 filter (550 nm) was used in order to count the hybridized cells, and the DM400 extraction filter was used for the DAPI-stained cells.

The following formula was used to calculate the concentration of cells C (cells/ml) in each sample:

$$C = N \times 15.56 \times 14\,873.74 \times (1000/q)$$

N: average number of cells counted per field of view
q: volume of hybridization mixture used
14 873.74: magnification constant
15.56: factor for all dilutions made Genus-specific 16S rRNA-targeted oligonucleotide probes labeled with the fluorescent dye Cy 3 which have previously been designed and validated were used to count important groups of bacteria. The probes used were Bif164, specific for *bifidobacterium* (Langedijk (1995), Appl Environ Microbiol 61, 3069-3075), Bac303, specific for *bacteroides* (Manz et al. (1996) Microbiology 142, 1097-1106), His150, specific for the *Clostridium histolyticum* subgroup and Erec482, specific for the *Clostridium coccoides-Eubacterium rectale* group (Franks et al. (1998) Appl Environ Microbiol 64, 3336-3345), Lab158, specific for *Lactobacillus/Enterococcus* (Harmsen et al. (1999) Microb Ecol Health Dis 11, 3-12), Ato291, specific for *Atopobium* cluster. The nucleic acid dye 4',6-diamidino-2-phenylindole (DAPI) was used for total cell counting (table 11)

TABLE 11

| Probe | Target genus | Sequence (5' to 3') | T-hybridization/ ° C. |
|---|---|---|---|
| Bif 164 | *Bifidobacterium* spp. | CATCCGGCATTACCACCC | 50 |
| Bac 303 | *Bacteroides* spp. | CCAATGTGGGGGACCTT | 45 |
| Chis 150 | *Clostridium histolyticum* group | TTTCCYTCTAATTATGGC GTATT | 50 |
| Lab 158 | *Lactobacillus/Enterococcus* spp. | GGTATTAGCATCTGTTTC CA | 50 |
| Ato 291 | *Atopobium* cluster | GGTCGGTCTCTCAACCC | 50 |
| Erec 482 | *Clostridium coccoides-E. rectale* group | GCTTCTTAGTCARGTAC CG | 52 |

Analysis of Short-Chain Fatty Acids:

Short-chain fatty acids (SCFA) in samples taken from various vessels of the bowel model were analyzed as described in Pereira et al., Appl. Environ Microbiol (2003) 69(8), 4743-4752. The samples were centrifuged (6000 g, 10 min) in order to remove bacteria and solids and then filtered through a polysulfone HPLC filter with a pore size of 0.2 µm. Then 200 µl of each filtered supernatant were diluted with 800 µl of acetonitrile (1:4) which contained 3.7 mM 2-ethylbutyric acid as internal standard. The fatty acids were determined by gas chromatography using a HP 5890 series II GC system provided with a fused silica packed capillary column (Permabond FFAP, Macherey Nagel, DE) (25 m×0.32 mm, film thickness 0.25 µm). Helium was used as carrier gas with a volumetric flow of 2.42 ml/min. The column temperature was 140° C. and the injector and detector temperature was 240° C. 5 minutes after injection of the sample, the column temperature was increased in steps of 20° C./min to 240° C. and the system was left to run for a further 5 minutes. The gas composition was analyzed using an HP 3365 series II ChemStation Apg-top Software, Version A0.03.34. The following acids were used as external standards, each with concentrations in the range from 0.5 to 40 mM: acetic acid, propionic acid, n-butyric acid, n-valeric acid, isovaleric acid (Fluka), isobutyric acid (Fluka) and n-caproic acid. Unless indicated otherwise, all the acids were purchased from Sigma and were more than 99% pure. The SCFA concentrations were calculated using an internal standard calibration and expressed in mM per liter.

2. Results

The following inulins were tested in the bowel model described above:
Inulin of the invention: DPw=77-81
Comparison sample: Raftinline HP® (Orafti), DPw=33

Comparison was made between the second steady state (SS2) and the first steady state (SS1) and the data were analyzed using Student's t test.

Figure 6:
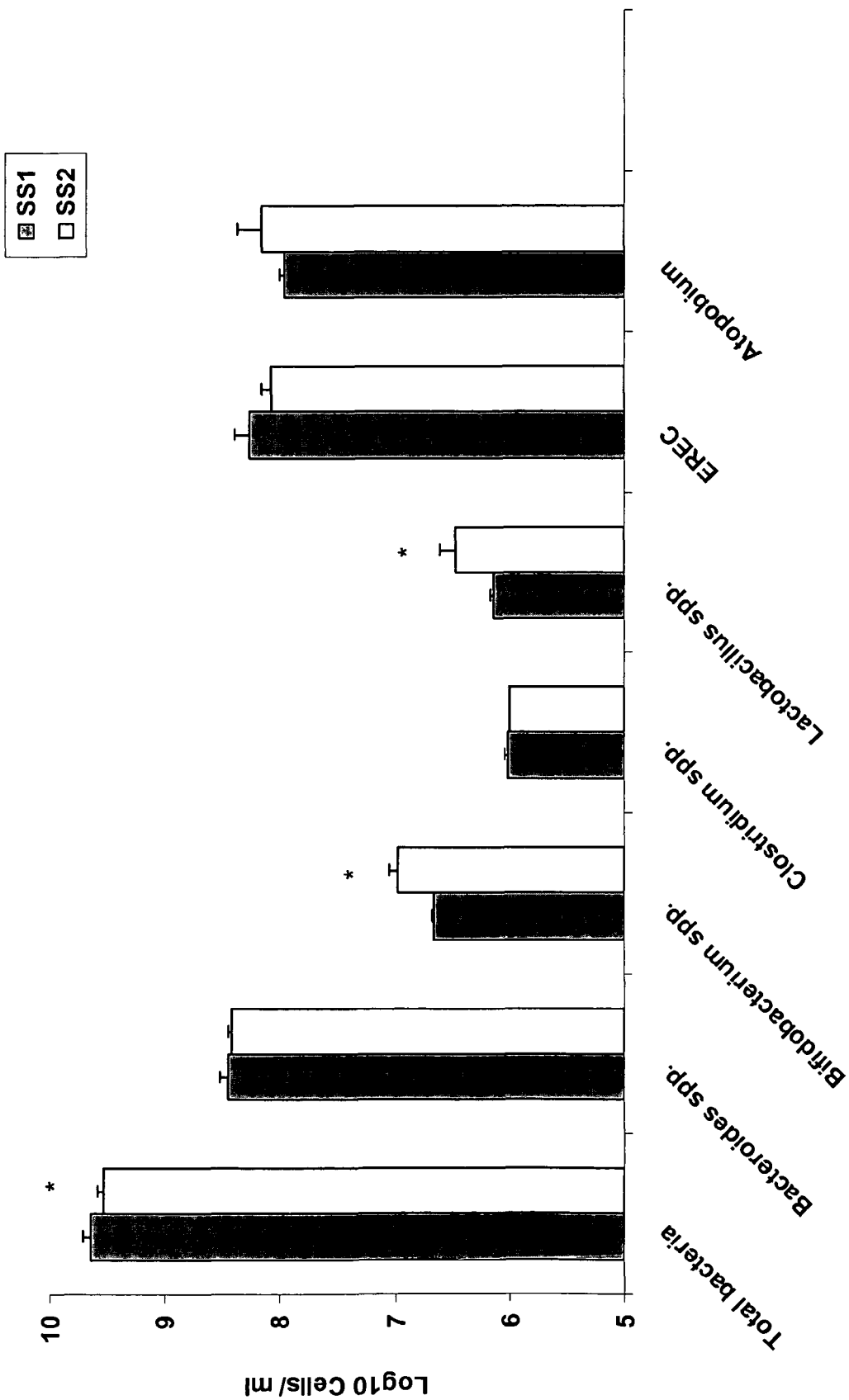
FIGS. 6 and 7 show corresponding comparisons for vessels 2 (V2) and 3 (V3).
Figure 7:
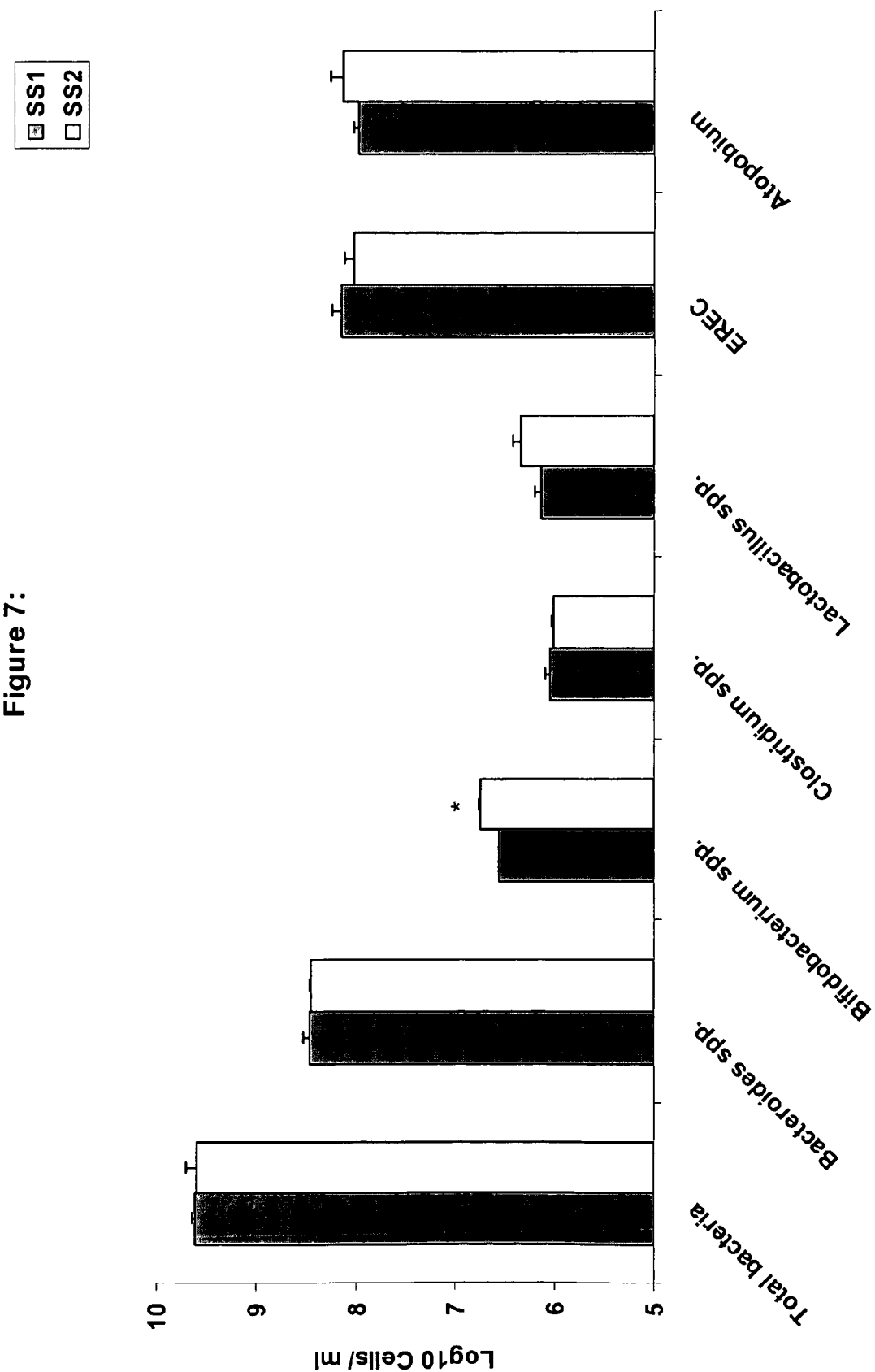

FIG. 5 shows the comparison of the bacterial population in vessel 1 (V1) between steady state 1 (SS1) and steady state 2 (SS2) after treatment with inulin of the invention. FIGS. 6 and 7 show corresponding comparisons for vessel 2 (V2) and 3 (V3).

Figure 8:
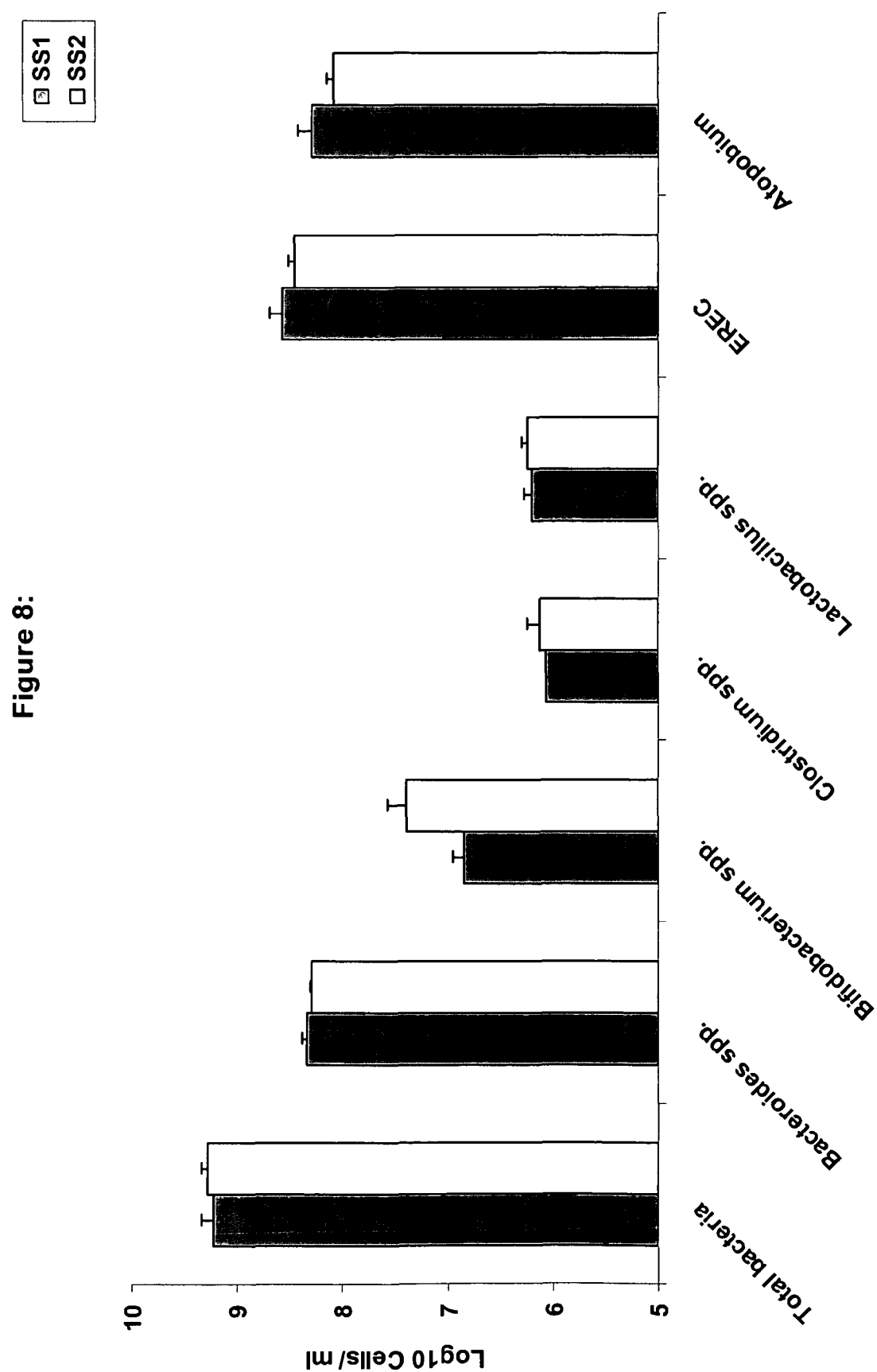
FIG. 8 shows the comparison of the bacterial population in vessel 1 (V1) between steady state 1 (SS1) and steady state 2 (SS2) after treatment with the comparative sample.
Figure 9:
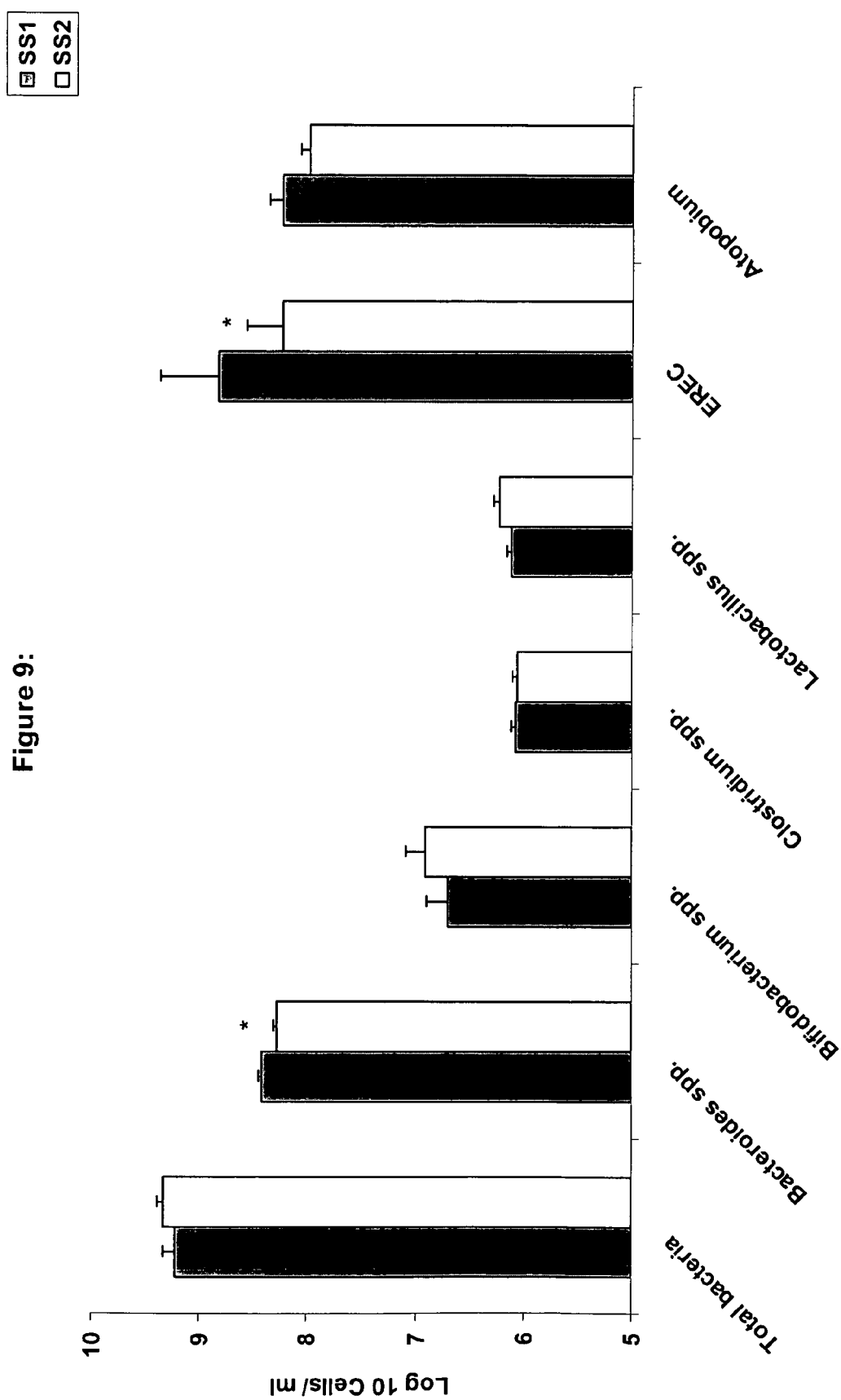
FIG. 9 and FIG. 10 show corresponding comparison for vessels 2 (V2) and 3 (V3).
Figure 10:
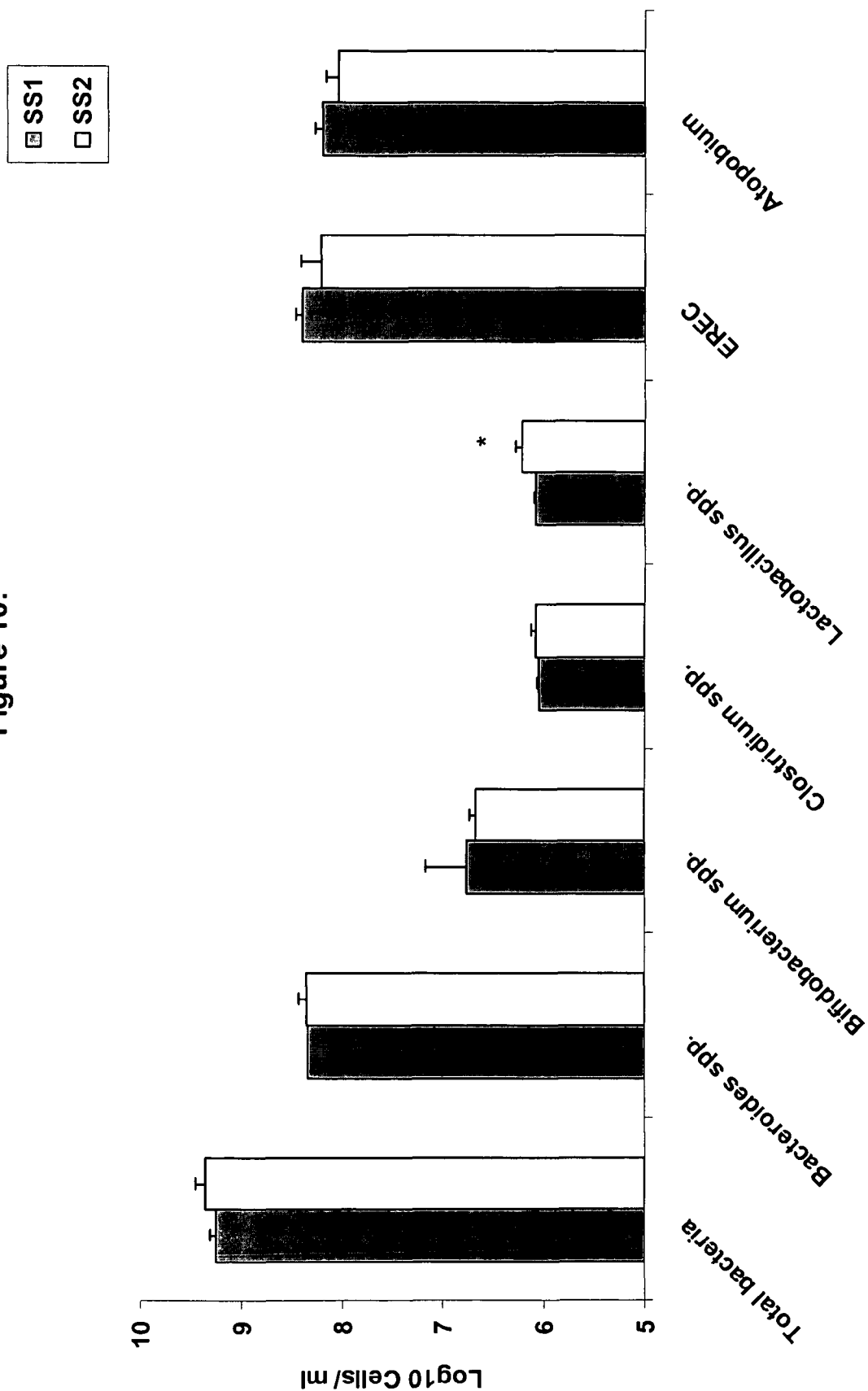

FIG. 8 shows the comparison of the bacterial population in vessel 1 (V1) between steady state 1 (SS1) and steady state 2 (SS2) after treatment with the comparative sample. FIGS. 9 and 10 show corresponding comparisons for vessel 2 (V2) and 3 (V3).

A bifidogenic response was observed after addition of the inulin of the invention to the bowel model. The level of increase was significant in all three vessels for bifidobacteria and significant for lactobacillae in vessel 2 ($P<0.05$). The Clostridia levels remained unchanged. With the comparative sample there was observed to be an increase in bifidobacteria in vessel 1, but this was not significant. The population of lactobacillae in vessel 3 was significantly higher ($P<0.05$) but no change was observed in the population of Clostridia. The *Bacteroides* and the *Clostridium* coccoides-E. rectale group was significantly lower in vessel 2 ($P<0.05$).

Figure 11:
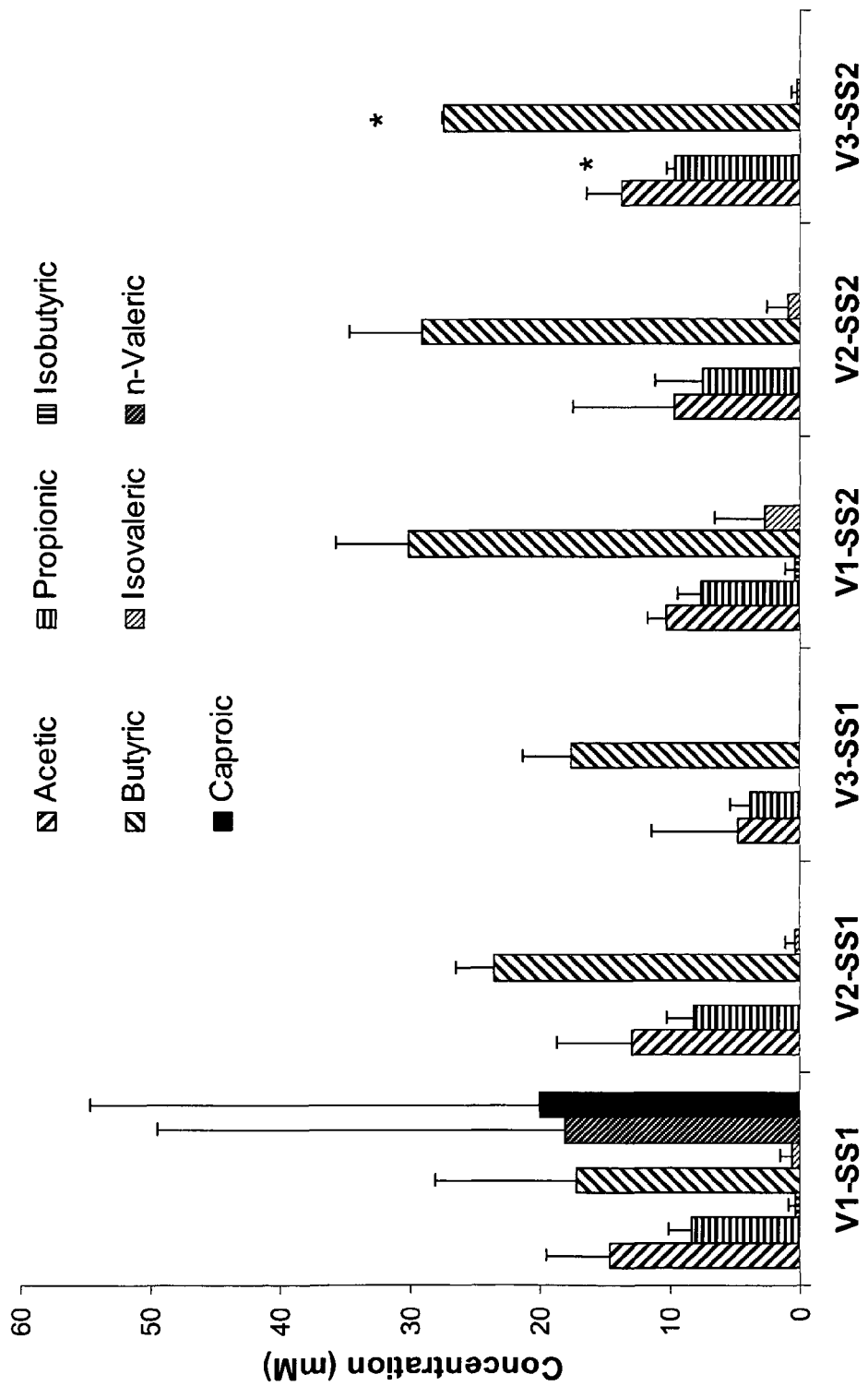
FIG. 11 shows comparison of the concentration of short-chain fatty acids (SCFA) in all vessels between steady state 1 (base line) (SS1) and steady state (2) after treatment with inulin of the invention.

FIG. 11 shows a comparison of the concentration of short-chain fatty acids (SCFA) in all vessels between steady state 1 (base line) (SS1) and steady state 2 (SS2) after treatment with inulin of the invention. The individual fatty acids are plotted in each case as bile diagram for each vessel and steady state (e.g. V1-SS1). From left to right: acetic acid, propionic acid, isobutyric acid, butyric acid, isovaleric acid, n-valeric acid, caproic acid.

Figure 12:
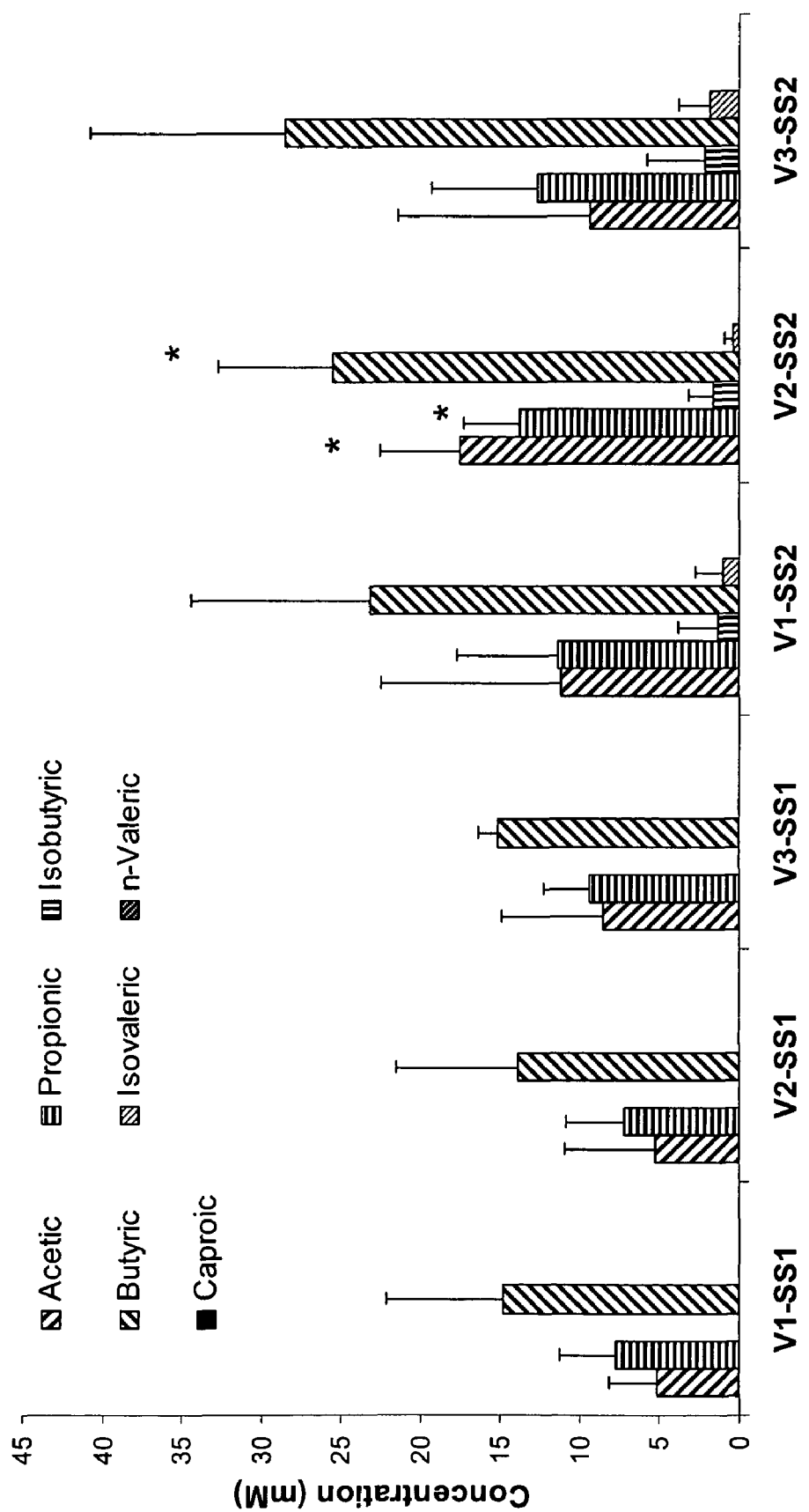
FIG. 12 shows the comparison of the concentrations of short-chain fatty acid (SCFA) in all vessels between steady state 1 (base line) (SS1) and steady state 2 (SS2) after treatment with the comparative sample.

FIG. 12 shows the comparison of the concentration of short-chain fatty acids (SCFA) in all vessels between steady state 1 (base line) (SS1) and steady state 2 (SS2) after treatment with the comparative sample.

Addition of the inulin of the invention in the bowel model led to a significant increase in the butyrate and propionate concentrations in vessel 3 (V3) ($P<0.05$). The butyrate concentration did not increase significantly in the other vessels. Addition of the comparative sample in the bowel model led to an increase in the concentration of acetate, propionate and butyrate in all vessels, but this was significant only in vessel 2 (V2).

The in vivo test reveals that the inulin of the invention is a strong potential prebiotic because both the number of bifidobacteria and the number of lactobacillae increased in all three vessels. This was accompanied by an increase in the butyrate concentration in all vessels and a significant increase in butyrate and propionate in vessel 3. The increase in butyrate and propionate in vessel 3 is a strong indication that the inulin of the invention exhibits a prebiotic effect in the posterior part of the large bowel. This is advantageous because the majority of bowel cancers arises in the distal region of the large bowel/in the rectum.

8. Production of Yoghurt

Methods

Yoghurt was prepared in 700 g batches. Milk was standardized to different contents of milk solids without fat (MSNF) in the range 11.0-14.0 percent by weight based on the total composition. The amounts of inulin (inulin of the invention and comparative inulin Beneo HP® from Orafti) were adjusted to 0.0 to 4.5% by weight. The yoghurt recipes are listed in table 12. The inulin of the invention (very long chain inulin, abbreviated to VLCI hereinafter) corresponded to the inulin from example 1/table 2 and had an average degree of polymerization DPw of 75, the comparative sample Beneo HP® had a DPw of 34. All percentages relate to percent by weight based on the total composition, unless indicated otherwise.

The dry ingredients were mixed together in order to facilitate the dispersion of inulin and fat-free dry milk, and then added to the milk with moderate shearing in order to form the yoghurt base. The standardized base was maintained at 4° C. for 3 hours so that the fat-free dry milk could dissolve completely. Each batch was pasteurized at 80° C. for 30 minutes, rapidly cooled to 44° C. and inoculated with Yo-Flex 88 (Streptococcus thermophilus and *Lactobacillus* delbrueckii, from Chr. Hansen Inc.) in a concentration of 3.6 g/l. For pot-fermented yoghurt (custard style yoghurt), inoculated base was poured into the final packs before incubation. Stirred yoghurt was incubated in large tanks. The base mixes were incubated at 44° C. for 4-6 hours until they reached pH 4.5 (initial pH about 6.8). When the yoghurt reached pH 4.5, the custard-style yoghurt samples were cooled to 4° C. and maintained thereat for 48 hours in order to reach the maximum viscosity. Stirred samples were cooled to 35° C., mixed with low shearing, packaged in plastic pots, cooled to 4° C. and maintained thereat for 48 hours in order to reach the maximum viscosity. The viscosity was measured with a Brookfield viscometer with a heliopath adapter.

TABLE 12

(all numerical data in % by weight based on the total mass, excluding viscosity)

| | Test | | | | | | | | | |
|---|---|---|---|---|---|---|---|---|---|---|
| | 1 | 2 | 3 | 4 | 5 | 6 | 7 | 8 | 9 | 10 |
| | Variation in inulin content | | | | | | Less solid with 3.5% inulin | | | |
| a) Data on the individual ingredients | | | | | | | | | | |
| 2% milk | — | — | — | — | 69.84 | — | — | — | — | — |
| Sugar | — | — | — | — | — | — | — | — | — | — |
| Skimmed milk | 89.05 | 89.92 | 90.88 | 91.79 | 23.38 | 89.05 | 90.74 | 91.58 | 92.43 | 90.74 |

TABLE 12-continued (all numerical data in % by weight based on the total mass, excluding viscosity)

| | | | | | | | | | |
|---|---|---|---|---|---|---|---|---|---|
| Fat-free dry milk | 5.81 | 5.86 | 5.93 | 5.99 | 6.08 | 5.81 | 5.01 | 4.13 | 3.25 | 5.01 |
| Stabilizer CC723 | 0.67 | 0.68 | 0.68 | 0.69 | 0.70 | 0.67 | 0.68 | 0.69 | 0.70 | 0.68 |
| Beneo HPX | — | — | — | — | — | 4.47 | — | — | — | 3.57 |
| Inulin of the invention (VLCI) | 4.47 | 3.53 | 2.51 | 1.53 | — | — | 3.57 | 3.60 | 3.63 | — |
| b) Data on the solids | | | | | | | | | | |
| Milk solids | 13.41 | 13.54 | 13.69 | 13.82 | 14.04 | 13.41 | 12.79 | 12.03 | 11.25 | 12.79 |
| Inulin | 4.47 | 3.53 | 2.51 | 1.53 | — | 4.47 | 3.57 | 3.60 | 3.63 | 3.57 |
| Fat | — | — | — | — | 1.40 | — | — | — | — | — |
| Total solids | 17.88 | 17.08 | 16.20 | 15.36 | 15.44 | 17.88 | 16.36 | 15.63 | 14.88 | 16.36 |
| c) Qualitative data | | | | | | | | | | |
| Solids | H | H | H | H | H | H | M | L | VL | M |
| Inulin | H | M | L | VL | O | H(B) | M | M | M | M(B) |
| Fat | O | O | O | O | M | O | O | O | O | O |
| Stabilizer | H | H | H | H | H | H | H | H | H | H |
| Sugar | O | O | O | O | O | O | O | O | O | O |
| | H = high | M = moderate | L = low | O = zero | VL = very low | | | | | |
| Viscosity (relative) | 7250 | 5550 | 4666 | 3400 | 3300 | 3400 | 4690 | 4275 | 3860 | 3175 |

| | Test | | | | | | | |
|---|---|---|---|---|---|---|---|---|
| | 11 | 12 | 13 | 14 | 15 | 16 | 17 | 18 |
| | Sugar | | | | | No stabilizer | | |
| a) Data on the individual ingredients | | | | | | | | |
| 2% milk | — | — | — | 70.33 | — | 67.62 | — | 71.00 |
| Sugar | 3.87 | 3.90 | 4.04 | — | — | 4.08 | — | — |
| Skimmed milk | 85.61 | 86.42 | 89.45 | 23.55 | 90.54 | 22.64 | 91.37 | 23.77 |
| Fat-free dry milk | 5.58 | 5.64 | 5.83 | 6.12 | 5.90 | 4.98 | 5.04 | 5.23 |
| Stabilizer CC723 | 0.64 | 0.65 | 0.67 | — | — | 0.68 | — | — |
| Beneo HPX | — | — | — | — | — | — | — | — |
| Inulin of the invention (VLCI) | 4.29 | 3.40 | — | — | 3.56 | — | 3.59 | — |
| b) Data on the solids | | | | | | | | |
| Milk solids | 12.89 | 13.02 | 13.47 | 14.14 | 13.64 | 12.73 | 12.88 | 13.36 |
| Inulin | 4.29 | 3.40 | — | — | 3.56 | — | 3.59 | — |
| Fat | — | — | — | 1.41 | — | 1.35 | — | 1.42 |
| Total solids | 21.05 | 20.31 | 17.51 | 15.55 | 17.19 | 18.15 | 16.47 | 14.78 |
| c) Qualitative data | | | | | | | | |
| Solids | H | H | H | H | H | M | M | M |
| Inulin | H | M | O | O | M | O | M | O |
| Fat | O | O | O | H | O | H | O | H |
| Stabilizer | H | H | H | O | O | H | O | O |
| Sugar | H | H | H | O | O | H | O | O |
| Viscosity (relative) | 4750 | 5183 | 2950 | 3250 | 6000 | 2550 | 5500 | 2825 |

Figure 13:
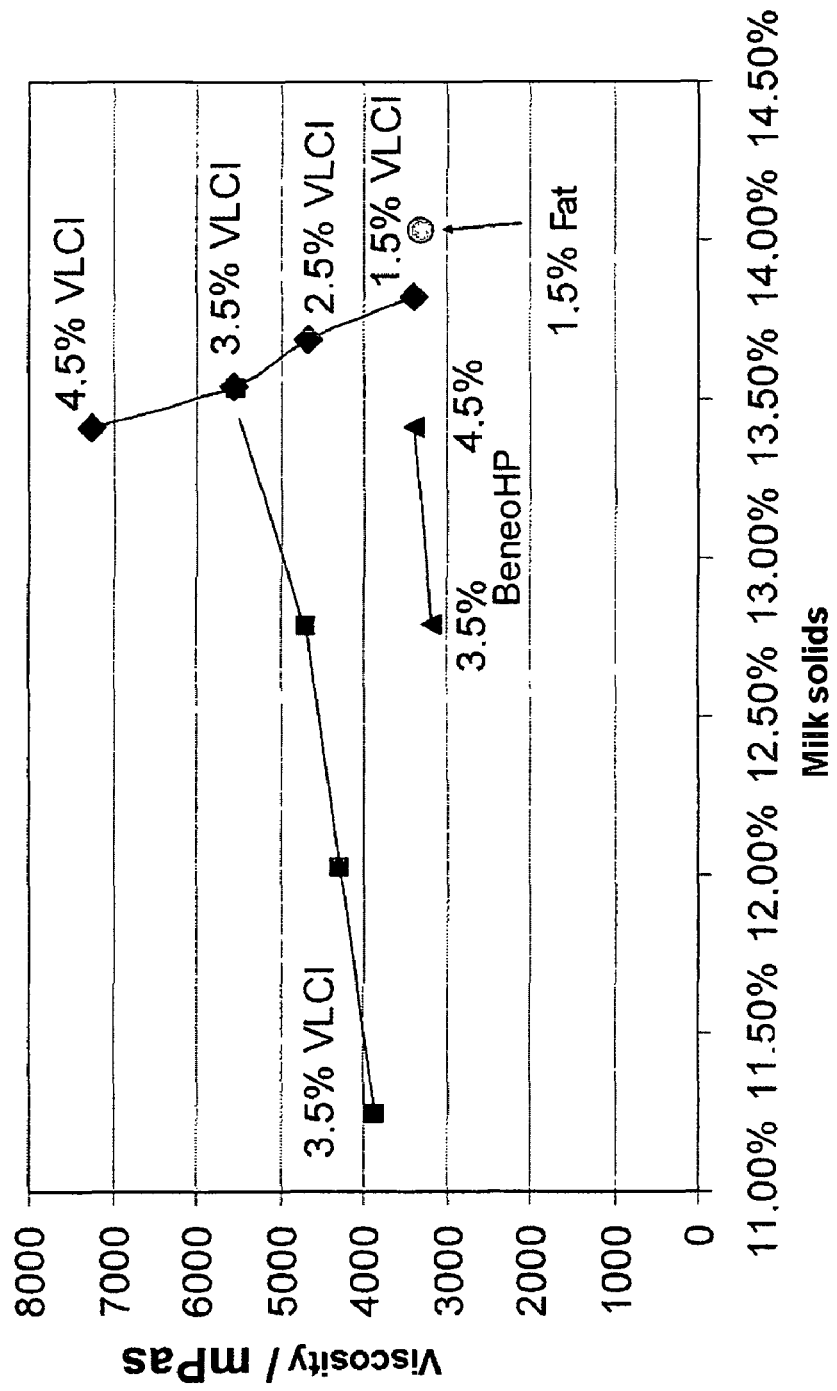
FIG. 13 shows the effects of inulin and milk solids on the yogurt viscosity.

Results:

FIG. 13 shows the effects of inulin and milk solids on the yoghurt viscosity. The inulin of the invention (VLCI) developed a significant viscosity in fat-free yoghurt, the viscosity levels reached with 4.5% VLCI being twice as high as those of a yoghurt with 1.5% fat without any inulin. The right-hand curve in FIG. 13 shows the dramatic change in viscosity when the VLCI contents in the yoghurt with about 13.5% milk solids rise from 1.5% to 4.5%. By comparison therewith, a change in the content of Beneo HP® had an only insignificant influence on the viscosity, even when the content of milk solids changed by 1%. The curve top left in FIG. 13 demonstrates the effect of increasing milk solids in yoghurt which contains 3.5% VLCI. In general, an increase of 1% in VLCI increased the viscosity of the fat-free yoghurt by approximately 30%, whereas Beneo HP® had a very much smaller effect on the viscosity. Depending on the content of milk solids, the amount of VLCI necessary to generate the viscosity level of a comparative yoghurt with 1.5% fat was 1.5-3.5%. At least 3.5% of Beneo HP® were necessary to achieve the viscosity level of a comparative yoghurt with 1.5% fat.

In a further test, 2.5% VLCI and 4.5% Beneo HP® were mixed in a fat-free yoghurt. A reduced fat yoghurt with 1.5% fat was used as comparison. The sample with VLCI had a higher viscosity than the two comparative samples with Beneo HP® and 1.5% fat, as shown in the table below.

TABLE 13

| Amount of inulin | Viscosity/relative |
|---|---|
| 2.5% VLCI | 4666 |
| 4.5% Beneo HP ® | 3400 |
| 1.5% fat | 3300 |

VLCI is unambiguously more effective at changing the texture of fat-free yoghurt than Beneo HP®, since higher viscosities were achieved with lower contents. This opens up the possibility of employing inulin more economically in yoghurt while maintaining an inulin content necessary to achieve a good bulking effect. In the above experiments, minimum amounts of 3 g of inulin per portion were maintained as the amount necessary for a bulking effect.

Table 14 shows further tests with pot-fermented yoghurt (custard style). Production took place as indicated previously.

It is evident that a spray-dried inulin of the invention has a particularly strong viscosity-increasing effect compared with the freeze-dried and drum-dried inulins. 2.5% spray-dried or drum-dried inulin of the invention still bring about a greater increase in viscosity than 4.5% inulin from the comparative example.

Table 15 shows tests with unstirred, pot-fermented yoghurt (custard) and with stirred yoghurt. Samples A-D were fermented normally. One portion of each sample was mixed with gentle shearing while the yoghurt was still warm (37-40° C.). The stirred and unstirred (custard) preparations were analyzed for the viscosity of each sample after 48 hours. Samples E-I were again fermented normally, but the stirred fractions E-G were mixed warm, as above, and sucrose was added during the mixing process. Samples H and I were mixed after the temperature had fallen to 10° C., in order to investigate the temperature effect on the inulin viscosity and yoghurt viscosity.

Addition of the spray-dried inulin of the invention (test C) increased the viscosity in the stirred and custard preparations, with the viscosity of whole-fat yoghurt (test D) being reached. In the second series (tests E-I), the viscosity was about the same on addition of the comparative inulin Beneo HP® as after addition of the inulin of the invention, but the product from test F was granular and the smoothness was low. A further observation was that in all experiments there was formation of a 5 mm layer of denatured whey protein on the bottom of the fermentation vessel—with the exception of the examples in which inulin of the invention was added. This is an indication that the inulin of the invention has beneficial effects on yoghurt stability.

TABLE 14

|  | Comparative example 4.5% commercial inulin | Example 2.5% inulin freeze-dried | Example 2.5% inulin drum-dried | Example 2.5% inulin spray-dried | Comparative example 1.5% fat | Comparative example 3.35% fat |
|---|---|---|---|---|---|---|
| a) Data on individual ingredients |  |  |  |  |  |  |
| Whole milk | — | — | — | — | — | 95.91 |
| 2% milk | — | — | — | — | 71.85 | — |
| Sugar | — | — | — | — | — | — |
| Skimmed milk | 91.51 | 93.44 | 93.44 | 93.44 | 24.06 | — |
| Fat-free dry milk | 3.21 | 3.28 | 3.28 | 3.28 | 3.37 | 3.37 |
| Stabilizer CC723 | 0.69 | 0.70 | 0.70 | 0.70 | 0.72 | 0.72 |
| Beneo HPX ® | 4.59 | — | — | — | — | — |
| Inulin DPw = 75 | — | — | — | — | — | — |
| Inulin DPw = 81 freeze-dried | — | 2.58 | — | — | — | — |
| Inulin DPw = 81 drum-dried | — | — | 2.58 | — | — | — |
| Inulin DPw = 81 spray-dried | — | — | — | 2.58 | — | — |
| b) Data on solids |  |  |  |  |  |  |
| Milk solids | 11.14 | 11.37 | 11.37 | 11.37 | 11.67 | 11.67 |
| Inulin | 4.59 | 2.58 | 2.58 | 2.58 | — | — |
| Fat | — | — | — | — | 1.44 | 3.36 |
| Total solids | 15.73 | 13.95 | 13.95 | 13.95 | 13.11 | 15.03 |
| Viscosity (centipoises) | 302 500 | 292 500 | 338 750 | 362 500 | 281 250 | 320 000 |
| pH | 4.34 | 4.52 | 4.41 | 4.57 | 4.57 | 4.55 |

All data in percent based on the total mass, except in viscosity and pH

TABLE 15

| | Test | | | | | | | | |
|---|---|---|---|---|---|---|---|---|---|
| | A Comparison low-fat yogurt | B Comparison low-fat 2% Beneo HP | C Example low-fat 2% inulin DPw = 81, spray-dried | D Comparison whole-fat yogurt | E Comparison low-fat yogurt | F Comparison low-fat 2% Beneo HP | G Example low-fat 2% inulin DPw = 81, spray-dried | H Example whole-fat 2% inulin DPw = 81, spray-dried | I Comparison whole-fat yogurt |
| Viscosity custard [cPs] | 238 000 | 267 000 | 308 000 | 326 000 | 240 000 | 306 000 | 306 000 | | |
| Viscosity stirred [cPs] | 90 000 | 110 000 | 146 000 | 152 000 | 61 000 | 104 000 | 120 000 | 84 000 | 62 000 |
| Sucrose added | — | — | — | — | Yes | Yes | Yes | Yes | Yes |
| Milk solids | 11.67% | 11.44% | 11.44% | 11.67% | 10.99% | 10.78% | 10.78% | 11.44% | 11.67% |
| Inulin | — | 2.04% | 2.04% | — | — | 1.83% | 1.83% | 2.04% | — |
| Fat | 1.44% | 1.41% | 1.41% | 3.36% | 1.28% | 1.26% | 1.26% | 3.29% | 3.36% |
| Total solids | 13.11% | 14.89% | 14.89% | 15.03% | 12.27% | 13.88% | 13.88% | 16.77% | 15.03% |

The invention claimed is:

1. Inulin having a weight average degree of polymerization $DP_w$ of between 65 and 81, wherein said inulin is spray-dried.

2. The inulin of claim 1, wherein said inulin has a weight average degree of polymerization $DP_w$ of between 65 and 79.

3. The inulin of claim 1, wherein said inulin has a degree of branching of between 0.5 and 2.0 mol % of 2-1,6 linked fructose monomers based on all inulin monomers.

4. The inulin of claim 1, wherein the quotient between the weight average degree of polymerization and the number average degree of polymerization (DPw/DPn) of said inulin is less than 1.25.

5. The inulin of claim 1, wherein the quotient DPw/DPn of said inulin is less than 1.20.

6. The inulin of claim 1, wherein the quotient DPw/DPn of said inulin is less than 1.15.

7. The inulin of claim 1, wherein said inulin has a glucose content less than 2% by weight based on the total dry weight.

8. The inulin of claim 1, wherein said inulin has a glucose content less than 1% by weight based on the total dry weight.

9. The inulin of claim 1, wherein said inulin has a fructose content less than 2.5% by weight based on the total dry weight.

10. The inulin of claim 1, wherein said inulin has a fructose content less than 1.5% by weight based on the total dry weight.

11. The inulin of claim 1, wherein said inulin is in the form of particles with an average diameter of 100-250 μm.

12. A process for obtaining inulin comprising
a) comminuting artichoke roots,
b) obtaining an extract by treating the comminuted roots with water,
c) removing coloring constituents from the extract,
d) precipitating inulin from the extract,
e) reprecipitating the inulin at least once, and (f) and spray drying inulin,
wherein said inulin has a weight average degree of polymerization $DP_w$ of between 65 and 81.

13. The process as claimed in claim 12, further comprising an additional filtration step.

14. The process as claimed in claim 12 wherein the coloring constituents are removed in step c) by
 i) admixing magnesium ions ($Mg^{2+}$) to the plant extract,
 ii) admixing at least one alkaline component to the plant extract,
 iii) forming a precipitate, and
 iv) removing the precipitate which has formed from the plant extract.

15. The process as claimed in claim 14, further comprising admixing a magnesium salt in step i).

16. The process as claimed in claim 15, wherein the magnesium salt is magnesium chloride, magnesium sulfate, magnesium nitrate, magnesium acetate, or magnesium propionate.

17. The process as claimed in claim 14, wherein step i) is carried out at a temperature of 60-80° C.

18. The process as claimed in claim 14, wherein the amount of alkaline component is chosen so that the $OH^-:Mg^{2+}$ molar ratio set up is 2.2:1- 1.8:1.

19. The process as claimed in claim 14, wherein the alkaline component is an aqueous solution or suspension of an alkali metal hydroxide or alkaline earth metal hydroxide.

20. The process as claimed in claim 14, wherein the alkaline component is a suspension of calcium hydroxide.

21. A foodstuff comprising inulin as claimed in claim 1.

22. The foodstuff as claimed in claim 21, wherein said foodstuff is a dairy product, yoghurt, ice cream, milk-based soft ice, milk-based garnish, pudding, milkshake, egg custard, cheese, nutrition bar, energy bar, breakfast bar, confectionery, bakery product, cracker, cookie, biscuit, cereal chip, snack product, ice tea, soft ice made from fruit juice, diet drink, finished drink, sports drink, stamina drink, powdered drink mixture for dietary supplementation, infant and baby food, calcium-supplemented orange juice, bread, croissant, breakfast cereal, noodle, spread, sugar-free biscuit, sugar-free chocolate, calcium chew, meat product, mayonnaise, salad dressing, nut butter, deep-frozen meal, sauce, soup, or ready-to-serve meal.

23. The foodstuff as claimed in claim 21 wherein said foodstuff is an extrusion product.

24. A dietary supplement comprising inulin as claimed in claim 1.

25. A cosmetic preparation comprising inulin as claimed in claim 1.

26. A method for manufacture of a foodstuff comprising adding inulin as claimed in claim 1 to a foodstuff.

27. The method as claimed in claim 26, wherein said inulin acts as an additive with prebiotic properties, a texturizing agent, a stability enhancing agent, a viscosity-building agent, and/or a dietary fiber in said foodstuff.

28. The method as claimed in claim 26, wherein said inulin acts as a fat or oil substitute in said foodstuff.

29. A method for manufacture of a cosmetic preparation comprising adding inulin as claimed in claim 1 to a cosmetic preparation.

30. The method as claimed in claim 29, wherein said inulin acts as a texturizing agent, a stability enhancing agent, and/or a viscosity-building agent in said cosmetic preparation.

31. An aqueous paste comprising the inulin as claimed in claim 1.

32. A method for the manufacture of a foodstuff or a cosmetic preparation comprising adding the aqueous paste claimed in claim 31, wherein the inulin in the aqueous paste acts as a structure imparting component, a fat substitute, an oil substitute, a texturizing agent, a stability enhancing agent, and/or a viscosity-building agent in said foodstuffs or cosmetic preparations.

* * * * *